United States Patent
Nakamura et al.

(10) Patent No.: US 11,480,920 B2
(45) Date of Patent: Oct. 25, 2022

(54) IMAGE PROCESSING APPARATUS, EVALUATION SYSTEM, IMAGE PROCESSING PROGRAM, AND IMAGE PROCESSING METHOD

(71) Applicant: FUJIFILM Corporation, Tokyo (JP)

(72) Inventors: Sohichiro Nakamura, Ashigarakami-gun (JP); Sho Onozawa, Ashigarakami-gun (JP); Ryusuke Osaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/537,590

(22) Filed: Nov. 30, 2021

(65) Prior Publication Data
US 2022/0083004 A1    Mar. 17, 2022

Related U.S. Application Data

(63) Continuation of application No. PCT/JP2020/020027, filed on May 21, 2020.

(30) Foreign Application Priority Data

Jun. 28, 2019   (JP) .............................. JP2019-122482

(51) Int. Cl.
| | | |
|---|---|---|
| G03H 1/22 | (2006.01) | |
| G06T 5/50 | (2006.01) | |
| G06T 7/00 | (2017.01) | |

(52) U.S. Cl.
CPC ............. *G03H 1/2294* (2013.01); *G06T 5/50* (2013.01); *G06T 7/0012* (2013.01);
(Continued)

(58) Field of Classification Search
CPC .. G03H 1/2294; G03H 1/0443; G03H 1/0866; G03H 2001/005;
(Continued)

(56) References Cited

U.S. PATENT DOCUMENTS

| | | | | |
|---|---|---|---|---|
| 8,885,913 B2 * | 11/2014 | Basiji | .................... | G06V 20/695 |
| | | | | 356/326 |
| 11,092,532 B2 * | 8/2021 | Singh | .................... | G03H 1/0866 |
| (Continued) | | | | |

FOREIGN PATENT DOCUMENTS

| | | |
|---|---|---|
| JP | 2003-156427 A | 5/2003 |
| JP | 2015-500475 A | 1/2015 |
| (Continued) | | |

OTHER PUBLICATIONS

Villone et al. "Full-angle tomographic phase microscopy of flowing quasi-spherical cells." Lab on a Chip 18.1 (2018): 126-131. (Year: 2018).*

(Continued)

*Primary Examiner* — Boubacar Abdou Tchoussou
(74) *Attorney, Agent, or Firm* — Birch, Stewart, Kolasch & Birch, LLP

(57) ABSTRACT

An image processing apparatus includes an acquisition unit that acquires a hologram obtained by imaging a plurality of granules contained within an imaging visual field, a generation unit that generates, from the hologram, phase difference images at positions different from each other in an optical axis direction in a case in which the hologram is captured, a specifying unit that specifies a plurality of image ranges in a direction of a plane intersecting the optical axis direction, which correspond to the plurality of granules, in an averaged image obtained by averaging at least some of the phase difference images, and an extraction unit that extracts the phase difference image at a center position of a corresponding granule in the optical axis direction for each of the plurality of image ranges.

11 Claims, 14 Drawing Sheets

(52) U.S. Cl.
CPC ............... *G03H 2226/02* (2013.01); *G06T 2207/20216* (2013.01); *G06T 2207/30024* (2013.01)

(58) Field of Classification Search
CPC . G03H 2001/0445; G06T 5/50; G06T 7/0012; G06T 2207/20216; G06T 2207/30024; G06V 10/89; G06V 20/698; G06V 10/44
See application file for complete search history.

(56) References Cited

U.S. PATENT DOCUMENTS

| | | |
|---|---|---|
| 2013/0148182 A1 | 6/2013 | Yu et al. |
| 2014/0030729 A1* | 1/2014 | Basiji ................. G01N 21/6458 435/6.14 |
| 2014/0333929 A1 | 11/2014 | Sung et al. |
| 2014/0376816 A1 | 12/2014 | Lagae et al. |
| 2015/0056607 A1 | 2/2015 | Jooris et al. |
| 2017/0284926 A1 | 10/2017 | Perraut et al. |
| 2020/0116617 A1* | 4/2020 | Singh ..................... G01N 15/147 |
| 2020/0311465 A1* | 10/2020 | Yellin ..................... G06V 10/82 |
| 2021/0199552 A1* | 7/2021 | Van Oostrum .... G01N 15/0211 |
| 2021/0209337 A1* | 7/2021 | Ozcan ................. G01N 15/1475 |

FOREIGN PATENT DOCUMENTS

| | | |
|---|---|---|
| JP | 2015-510592 A | 4/2015 |
| JP | 2016-511435 A | 4/2016 |
| JP | 2016-133466 A | 7/2016 |
| JP | 2018-507392 A | 3/2018 |
| WO | WO 2019/099592 A1 | 5/2019 |

OTHER PUBLICATIONS

International Preliminary Report on Patentability and Written Opinion of the International Searching Authority for International Application No. PCT/JP2020/020027, dated Jan. 6, 2022, with an English translation.

International Search Report for International Application No. PCT/JP2020/020027, dated Jul. 7, 2020, with an English translation.

Kemmler et al., "Noninvasive time-dependent cytometry monitoring by digital holography," Journal of Biomedical Optics, vol. 12, No. 6, 2007, pp. 064002-1-064002-10, 10 pages total.

Extended European Search Report for European Application No. 20833156.1, dated Jul. 12, 2022.

* cited by examiner

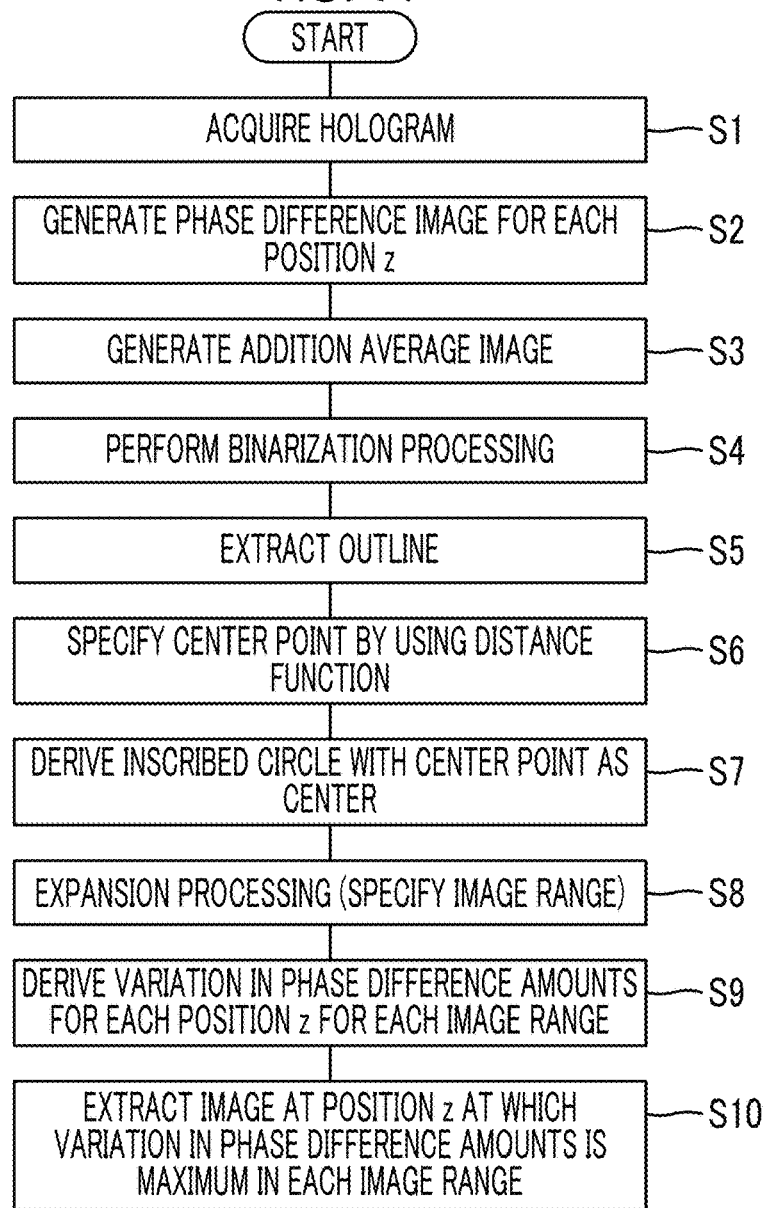
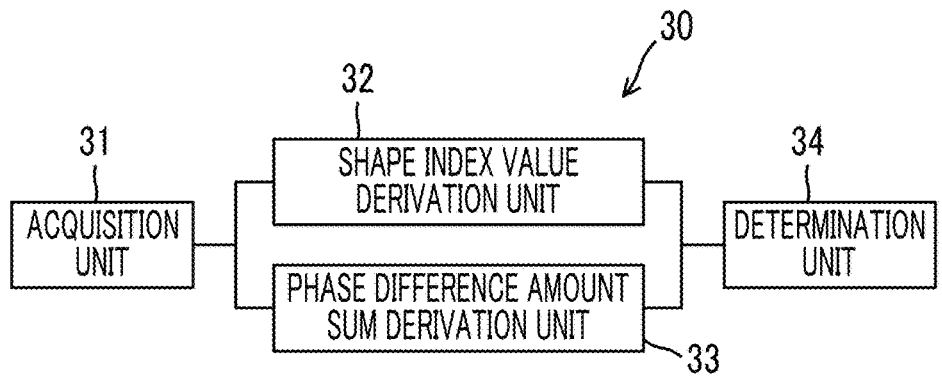

IMAGE PROCESSING APPARATUS, EVALUATION SYSTEM, IMAGE PROCESSING PROGRAM, AND IMAGE PROCESSING METHOD

CROSS-REFERENCE TO RELATED APPLICATIONS

This application is a Continuation of PCT International Application No. PCT/JP2020/020027 filed on May 21, 2020, which claims priority under 35 U.S.C § 119(a) to Japanese Patent Application No. 2019-122482 filed on Jun. 28, 2019. Each of the above application(s) is hereby expressly incorporated by reference, in its entirety, into the present application.

BACKGROUND OF THE INVENTION

1. Field of the Invention

The disclosed technology relates to an image processing apparatus, an evaluation system, an image processing program, and an image processing method.

2. Description of the Related Art

For example, the following technology is known as technology for evaluating or determining a state of a cell. For example, JP2016-511435A discloses a 3D holographic imaging system for a plurality of cells which continuously flow in a microfluidic channel. In this imaging system, a laser beam is used to measure a plurality of angular spectra scattered from the plurality of cells flowing in a line, the line within the microfluidic channel is focused. For measurements of a plurality of complex scattered fields, off-axis digital holography is used to allow one-shot recording of the field for each position in a sample. The microfluidic channel configured to reduce cell tumbling and allow use of a high NA condenser lens and an objective lens are used to transport a substance over a real visual field of the system. For data reconstruction, in order to reduce a plurality of diffraction artifacts resulting from a plurality of defocused organelles in the plurality of cells and to reduce a plurality of artifacts due to a limited angular range of an incident beam, optical diffraction tomography is used to apply iterative constraint procedures.

JP2015-500475A discloses a device that sorts an object immersed in a flowing medium. The device comprises a holographic imaging unit and a fluid handling unit including a plurality of microfluidic channels. The microfluidic channel includes an imaging region for guiding the flowing medium along a corresponding holographic imaging element to image a moving object immersed in the flowing medium. The microfluidic channel includes a microfluidic switch disposed on the downstream of the imaging region in one outlet selected from a plurality of outlets to direct each object in the flowing medium in a controllable manner. The device comprises a processing unit adapted to a real-time characteristic evaluation of a holographic diffraction image obtained for each of the objects in a case of passing through any of the imaging regions. The characteristic evaluation takes into account traces of at least one predetermined object type, and the processing unit is configured to control the microfluidic switch on the downstream of the imaging region in response to the characteristic evaluation.

JP2016-133466A discloses a water quality examination system that measures the number of biological fine substances in a target water. This water quality examination system comprises a data processing unit that processes hologram data, which is data of interference fringes imaged by an image element. The data processing unit counts the number of biological fine substances by reproducing each acquired hologram data, and performs data processing of counting the number of images of biological fine substance, which is determined in a case of image reproduction of each hologram data.

SUMMARY OF THE INVENTION

As a culture method capable of mass production of cells, a three-dimensional culture method is known in which spheres, which are aggregates of the cells, are cultured in a state of being floated in a culture medium. In a manufacturing process of the cells by three-dimensional culture, the technology for non-destructively and easily evaluating a quality of the cells in a state of the sphere is required from the viewpoint of ease of process management.

In a case in which the flow cytometry in the related art is used as a sphere observation method, the spheres flowing in flow cells are observed one by one, and a huge amount of processing time is required for observation of all of a large number of spheres. In a system comprising an imaging apparatus that acquire the flow cells in which the spheres flow and the hologram of the spheres, in order to shorten the processing time, it is conceivable to image a plurality of spheres within the imaging visual field of the imaging apparatus. However, it is assumed that the plurality of spheres included in the imaging visual field are imaged in a state in which some of the plurality of spheres overlap with each other. In order to appropriately evaluate the state of an individual sphere from such an image, a method of specifying a region of each sphere from the image containing the plurality of spheres in a state of overlapping with each other is required. In addition, it is also necessary to consider which cross section image of the imaging apparatus in an optical axis direction is suitable for evaluating the state of the sphere.

The disclosed technology is to provide an image processing apparatus, an evaluation system, and an image processing program, and an image processing method that enable to appropriately perform an evaluation of a state of an individual granule by using a hologram obtained by imaging a plurality of granules contained within an imaging visual field.

An aspect of the disclosed technology relates to an image processing apparatus comprising an acquisition unit that acquires a hologram obtained by imaging a plurality of granules contained within an imaging visual field, a generation unit that generates, from the hologram, phase difference images at positions different from each other in an optical axis direction in a case in which the hologram is captured, a specifying unit that specifies a plurality of image ranges in a direction of a plane intersecting the optical axis direction, which correspond to the plurality of granules, in an averaged image obtained by averaging at least some of the phase difference images, and an extraction unit that extracts the phase difference image at a center position of a corresponding granule in the optical axis direction for each of the plurality of image ranges.

With the image processing apparatus according to the disclosed technology, it is possible to appropriately perform the evaluation of the state of individual granule by using the hologram obtained by imaging the plurality of granules contained within the imaging visual field.

The specifying unit may include an addition average image generation unit that generates, as the averaged image, an addition average image obtained by adding and averaging at least some of the phase difference images, an inscribed circle derivation unit that derives a plurality of inscribed circles inscribed in an outline corresponding to an outer edge of the granule in the addition average image with each point at which a distance from the outline is longer than those of other surrounding points as a center, and an expansion processing unit that performs expansion processing on each of the inscribed circles. As a result, it is possible to appropriately specify an extending region of the granules in the direction of the plane intersecting the optical axis direction.

The extraction unit may extract, as the phase difference image at the center position of the granule in the optical axis direction, a phase difference image having a maximum variation of phase difference amounts between pixels among the phase difference images at the positions different from each other in the optical axis direction. As a result, it is possible to extract the phase difference image in which the granule is focused.

The granule may be an aggregate of a plurality of cells.

Another aspect of the disclosed technology relates to an evaluation system comprising an imaging apparatus that captures a hologram in which a plurality of granules are contained within an imaging visual field, an image processing apparatus that performs image processing on the hologram, and an evaluation apparatus that outputs an evaluation result for each of the plurality of granules based on an image obtained by the image processing apparatus. The image processing apparatus includes an acquisition unit that acquires the hologram, a generation unit that generates, from the hologram, phase difference images at positions different from each other in an optical axis direction in a case in which the hologram is captured, a specifying unit that specifies a plurality of image ranges in a direction of a plane intersecting the optical axis direction, which correspond to the plurality of granules, in an averaged image obtained by averaging at least some of the phase difference images, and an extraction unit that extracts the phase difference image at a center position of a corresponding granule in the optical axis direction for each of the plurality of image ranges. The evaluation apparatus derives the evaluation result by using the phase difference image extracted by the extraction unit.

With the evaluation system according to the disclosed technology, it is possible to automatically and appropriately perform the evaluation of the state of individual granule by using the hologram obtained by imaging the plurality of granules contained within the imaging visual field.

The evaluation system according to the aspect of the disclosed technology may further comprise a flow passage through which the plurality of granules flow. It is preferable that the imaging apparatus be installed such that an entire region of the flow passage in a width direction is contained within the imaging visual field. As a result, it is possible to significantly shorten the processing time as compared with an evaluation method in the related art using flow cytometry.

Still another aspect of the disclosed technology relates to an image processing program causing a computer to execute a process comprising acquiring a hologram obtained by imaging a plurality of granules contained within an imaging visual field, generating, from the hologram, phase difference images at positions different from each other in an optical axis direction in a case in which the hologram is captured, specifying a plurality of image ranges in a direction of a plane intersecting the optical axis direction, which correspond to the plurality of granules, in an averaged image obtained by averaging at least some of the phase difference images, and extracting the phase difference image at a center position of a corresponding granule in the optical axis direction for each of the plurality of image ranges.

With the image processing program according to the disclosed technology, it is possible to automatically and appropriately perform the evaluation of the state of individual granule by using the hologram obtained by imaging the plurality of granules contained within the imaging visual field.

Still another aspect of the disclosed technology relates to an image processing method comprising acquiring a hologram obtained by imaging a plurality of granules contained within an imaging visual field, generating, from the hologram, phase difference images at positions different from each other in an optical axis direction in a case in which the hologram is captured, specifying a plurality of image ranges in a direction of a plane intersecting the optical axis direction, which correspond to the plurality of granules, in an averaged image obtained by averaging at least some of the phase difference images, and extracting the phase difference image at a center position of a corresponding granule in the optical axis direction for each of the plurality of image ranges.

With the image processing method according to the disclosed technology, it is possible to automatically and appropriately perform the evaluation of the state of individual granule by using the hologram obtained by imaging the plurality of granules contained within the imaging visual field.

According to the disclosed technology, as one aspect, the effect is provided that it is possible to automatically and appropriately perform the evaluation of the state of individual granule by using the hologram obtained by imaging the plurality of granules contained within the imaging visual field.

BRIEF DESCRIPTION OF THE DRAWINGS

FIG. 11 is a flowchart showing an example of a flow of image processing according to the embodiment of the disclosed technology.

FIG. 12 is a functional block diagram showing an example of a functional configuration of an evaluation apparatus according to the embodiment of the disclosed technology.

DESCRIPTION OF THE PREFERRED EMBODIMENTS

Figure 1:
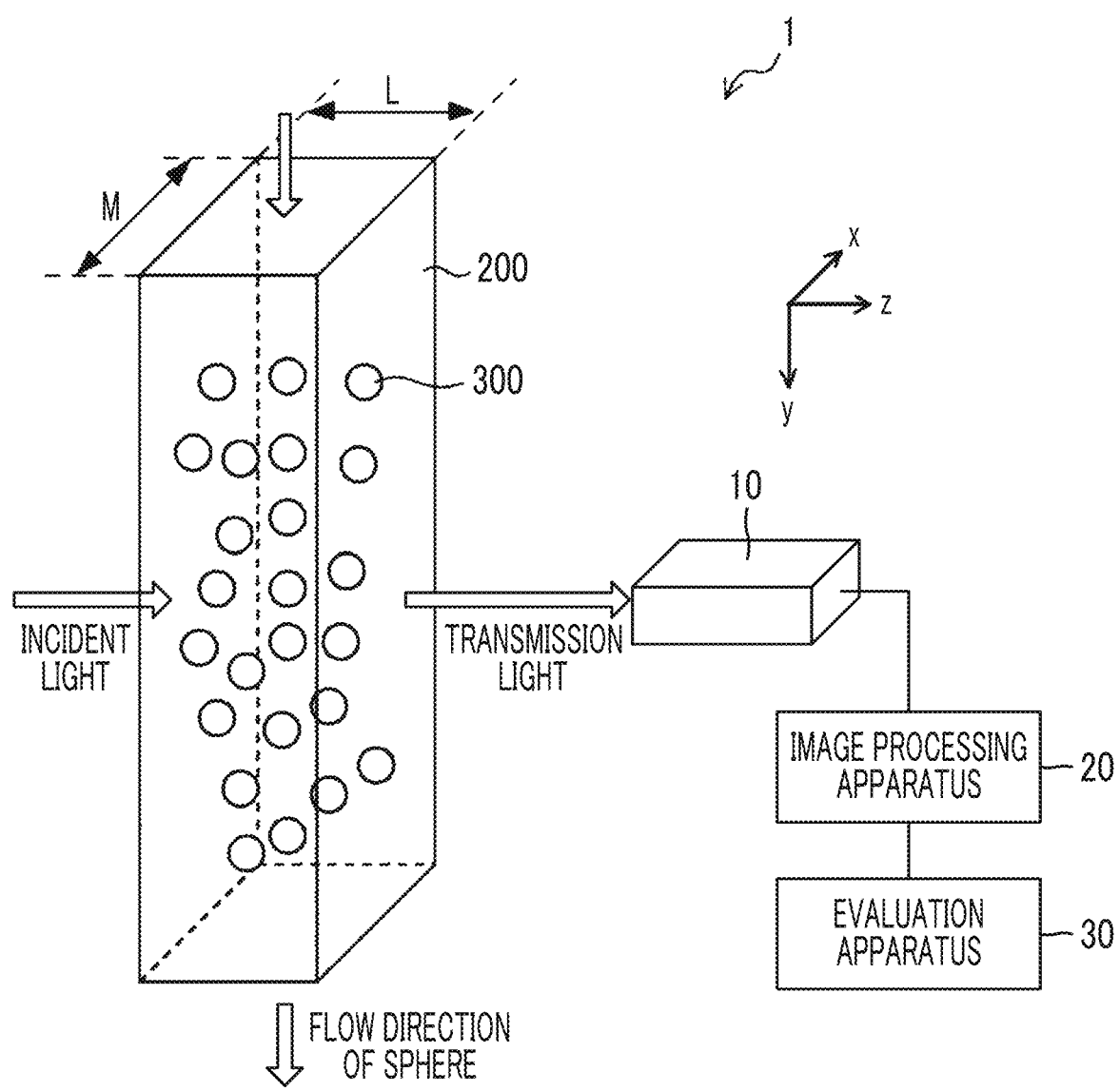
FIG. 1 is a diagram showing an example of a configuration of an evaluation system according to an embodiment of the disclosed technology.

Hereinafter, an example of an embodiment of the disclosed technology will be described with reference to the drawings. Note that in the drawings, the same reference numerals are given to the same or equivalent components and portions.

FIG. 1 is a diagram showing an example of a configuration of an evaluation system 1 according to the embodiment of the disclosed technology. The evaluation system 1 includes an imaging apparatus 10, an image processing apparatus 20, and an evaluation apparatus 30.

The imaging apparatus 10 captures a hologram in which a plurality of granules are contained within an imaging visual field. In the present embodiment, the imaging apparatus 10 captures the hologram of a plurality of spheres 300, which are aggregates of cells flowing inside a flow cell 200.

The flow cell 200 is constituted by a member having a light-transmitting property, and forms a flow passage through which the sphere 300 flows. In the present embodiment, a flow passage cross section of the flow cell 200 has a quadrangular shape, a width dimension M is, for example, about 10 mm, and a depth dimension L is, for example, about 3 mm. That is, an area of the flow passage cross section of the flow cell 200 is sufficiently larger than a size of the sphere 300 (for example, about 100 µm to 500 µm). Note that a shape and a size of the flow passage cross section of the flow cell 200 are not limited to those described above, and can be changed as appropriate. Note that in the following description, an optical axis direction of the imaging apparatus 10 is a z direction, a flow direction of the sphere 300 is a y direction, a width direction of the flow cell 200 is an x direction, and a plane orthogonal to the z direction is an xy plane.

It is desirable that the imaging apparatus 10 be installed such that the entire flow cell 200 in the width direction (x direction) is contained within the imaging visual field when all of the plurality of spheres 300 are examined. Therefore, the plurality of spheres 300 flowing in the flow cell 200 are contained within the imaging visual field of the imaging apparatus 10. The imaging apparatus 10 may continuously image the plurality of spheres 300 flowing inside the flow cell 200. As a result, all of the spheres 300 in culture that sequentially flow inside the flow cell 200 can be an imaging target. The imaging apparatus 10 may be, for example, a complementary metal oxide semiconductor (CMOS) camera.

Figure 2:
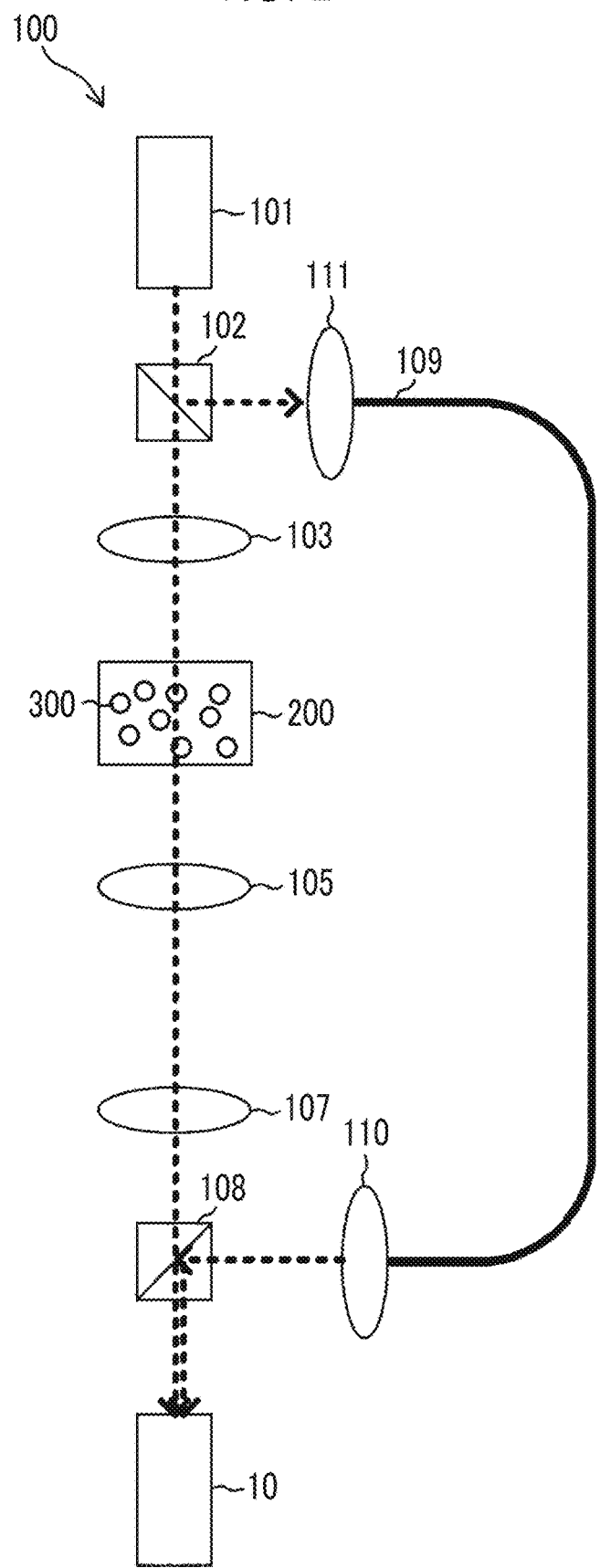
FIG. 2 is a diagram showing an example of a configuration of a hologram optical system according to the embodiment of the disclosed technology.

FIG. 2 is a diagram showing an example of a configuration of a hologram optical system 100 that acquires the hologram of the sphere by using known digital holography technology. The hologram optical system 100 includes an imaging apparatus 10. The digital holography technology is technology for imaging an image generated by interference between object light transmitted through or reflected by an object and reference light, which is coherent to the object light, by an image sensor, performing numerical calculation based on light propagation on the image obtained by imaging, and restoring a wave surface of light wave from the object. With the digital holography technology, it is possible to acquire three-dimensional information of the object without quantifying phase distribution of the object or mechanically moving a focal position.

The hologram optical system 100 includes a laser light source 101, beam splitters 102 and 108, collimating lenses 103, 110, and 111, an objective lens 105, an imaging lens 107, and the imaging apparatus 10. The flow cell 200 in which the sphere 300, which is the imaging target, flows is disposed between the collimating lens 103 and the objective lens 105.

For example, a HeNe laser having a wavelength of 632.8 nm can be used as the laser light source 101. A laser beam emitted from the laser light source 101 is divided into two laser beams by the beam splitter 102. One of the two laser beams is the object light and the other is the reference light. The object light is converted parallel light by the collimating lens 103, and then is emitted to the sphere 300 flowing inside the flow cell 200. The image of the object light transmitted through the sphere 300 is expanded by the objective lens 105. The object light transmitted through the objective lens 105 is converted into the parallel light again by the imaging lens 107, and then is imaged on an imaging surface of the imaging apparatus 10 via the beam splitter 108. On the other hand, the reference light is incident on an optical fiber 109 via the collimating lens 111 and is guided to the front of the collimating lens 110 by the optical fiber 109. The reference light emitted from the optical fiber 109 is converted into the parallel light by the collimating lens 110, and is incident on the imaging surface of the imaging apparatus 10 via the beam splitter 108. The hologram generated by the interference between the object light and the reference light is recorded by the imaging apparatus 10. Note that an off-axial optical system may be configured in which the optical axis directions of the object light and the reference light incident on the imaging surface of the imaging apparatus 10 are different from each other. The hologram of the sphere 300 imaged by the imaging apparatus 10 is stored in an image memory (not shown) provided in the imaging apparatus 10. The hologram of the sphere 300 stored in the image memory is supplied to the image processing apparatus 20. Note that the optical axis direction of the imaging apparatus 10 is an optical axis direction of the imaging system, and coincides with a direction in which the objective lens 105, the imaging lens 107, the beam splitter 108, and the imaging apparatus 10 are arranged.

Figure 3:
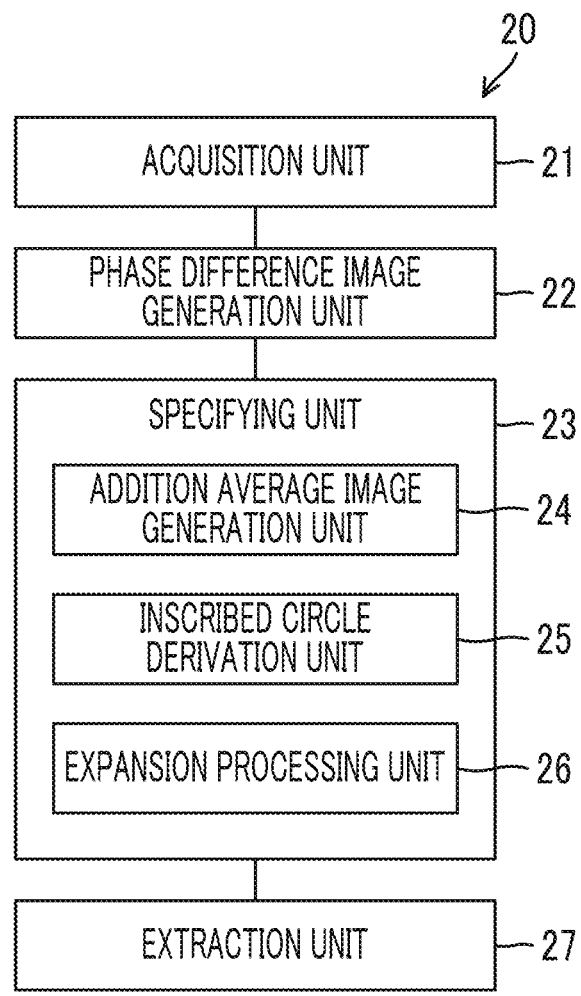
FIG. 3 is a functional block diagram showing a functional configuration of an image processing apparatus according to the embodiment of the disclosed technology.

FIG. 3 is a functional block diagram showing a functional configuration of the image processing apparatus 20. The image processing apparatus 20 performs the image processing on the hologram imaged by the imaging apparatus 10. The image processing apparatus 20 includes an acquisition unit 21, a phase difference image generation unit 22, a specifying unit 23, and an extraction unit 27. Note that the phase difference image generation unit 22 is an example of a generation unit in the disclosed technology. The specifying unit 23 includes an addition average image generation unit 24, an inscribed circle derivation unit 25, and an expansion processing unit 26.

The acquisition unit 21 acquires the hologram in which the plurality of spheres are contained within the imaging visual field, which is imaged by the imaging apparatus 10.

The phase difference image generation unit 22 generates phase difference images at positions z different from each other in the optical axis direction (z direction) of the imaging apparatus 10 from the hologram acquired by the acquisition unit 21. Note that the details of the phase difference image will be described below. The phase difference image generation unit 22 generates the phase difference image by, for example, performing each of the following processing.

Figure 4A:
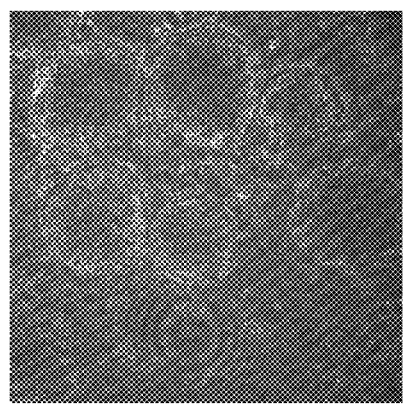
FIG. 4A shows an example of a hologram of a plurality of spheres according to the embodiment of the disclosed technology.
Figure 4B:
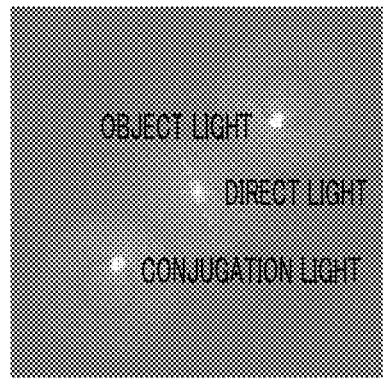
FIG. 4B shows an example of a Fourier transform image of the plurality of spheres according to the embodiment of the disclosed technology.

First, the phase difference image generation unit 22 performs a two-dimensional Fourier transform on the hologram of the plurality of spheres shown in FIG. 4A acquired by the imaging apparatus 10. FIG. 4B is an example of a Fourier transform image of the sphere obtained by this processing. FIG. 4B shows an image based on direct light, the object light, and conjugation light.

Next, the phase difference image generation unit 22 specifies the position of the object light by specifying an amount of deviation of the object light with respect to the direct light in the Fourier transform image, and extracts a complex amplitude component of only the object light by frequency filtering processing.

Next, the phase difference image generation unit 22 applies, for example, an angular spectrum method to restore the image showing the phase of the sphere at any spatial position. Specifically, the phase difference image generation unit 22 obtains an angular spectrum $U(f_x, f_y; 0)$ of the Fourier transform image of a wave surface $u(x, y; 0)$ captured by an image sensor surface of the imaging apparatus 10. Next, as described shown in Expression (1), the phase difference image generation unit 22 reproduces the wave surface at any position z in the optical axis direction (z direction) of the imaging apparatus 10 by multiplying the angular spectrum $U(f_x, f_y; 0)$ by a transfer function $H(f_x, f_y; z)$.

Here, the transfer function $H(f_x, f_y; z)$ is a frequency response function (Fourier transform of an impulse response function (Green's function)).

$$U(f_x, f_y; z) = U(f_x, f_y; 0) H(f_x, f_y; z), \quad (1)$$
$$H = e^{z \frac{2\pi}{\lambda} \sqrt{1-(\lambda f_x)^2-(\lambda f_y)^2}}$$

Next, as shown in Expression (2), the phase difference image generation unit 22 derives a solution $u(x, y; z)$ at the position z by performing an inverse Fourier transform on the wave surface $U(f_x, f_y; z)$ at the position z in the optical axis direction (z direction) of the imaging apparatus 10.

$$u(x, y; z) = F^{-1}[U(f_x, f_y; z)] \quad (2)$$
$$= F^{-1}[U(f_x, f_y; 0) H(f_x, f_y; z)]$$
$$= F^{-1}[F[u(x, y; 0)] H(f_x, f_y; z)]$$

Figure 4C:
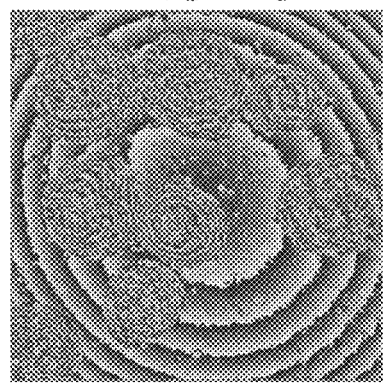
FIG. 4C is a diagram showing an example of a phase difference image before unwrapping of the plurality of spheres according to the embodiment of the disclosed technology.

Next, the phase difference image generation unit 22 generates the phase difference image by deriving a phase $\varphi$ for $u(x, y; z)$ as shown in Expression (3). FIG. 4C is an example of the phase difference image before unwrapping of the sphere obtained by the processing described above.

$$\phi = \arctan\left(\frac{\mathrm{Im}(u)}{\mathrm{Re}(u)}\right) \quad (3)$$

Figure 4D:
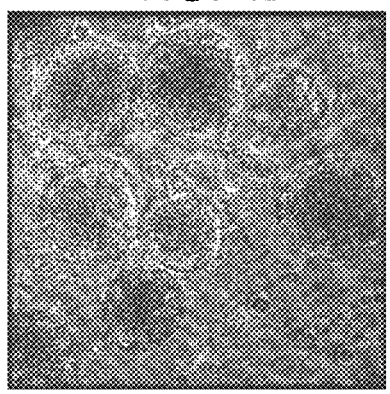
FIG. 4D is a diagram showing an example of an amplitude image of the plurality of spheres according to the embodiment of the disclosed technology.

Note that as shown in Expression (4), the phase difference image generation unit 22 may generate amplitude images at the positions z different from each other in the optical axis direction by deriving amplitude a for $u(x, y; z)$. FIG. 4D is an example of the amplitude images of the plurality of spheres.

$$a = \sqrt{(\mathrm{Re}(u))^2+(\mathrm{Im}(u))^2} \quad (4)$$

Figure 4E:
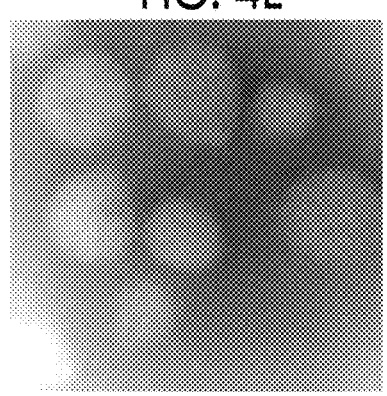
FIG. 4E is a diagram showing an example of a phase difference image after unwrapping of the plurality of spheres according to the embodiment of the disclosed technology.

The phase of the sphere before unwrapping shown in FIG. 4C is convoluted to a value of 0 to $2\pi$. Therefore, for example, by applying a phase connection (unwrapping) method such as unweighted least squares or Flynn's algorithm and joining the portions of 2π or more, a final phase difference image of the sphere as shown in FIG. 4E can be obtained. Note that many unwrapping methods have been proposed, and an appropriate method that does not cause phase inconsistency need only be appropriately selected.

The phase difference image generation unit 22 generates the phase difference images at the positions z different from each other in the optical axis direction (z direction) of the imaging apparatus 10 by performing the processing described above. A pitch width of the positions z in the optical axis direction (z direction) of the imaging apparatus 10 may be, for example, about 1 μm.

Figure 5:
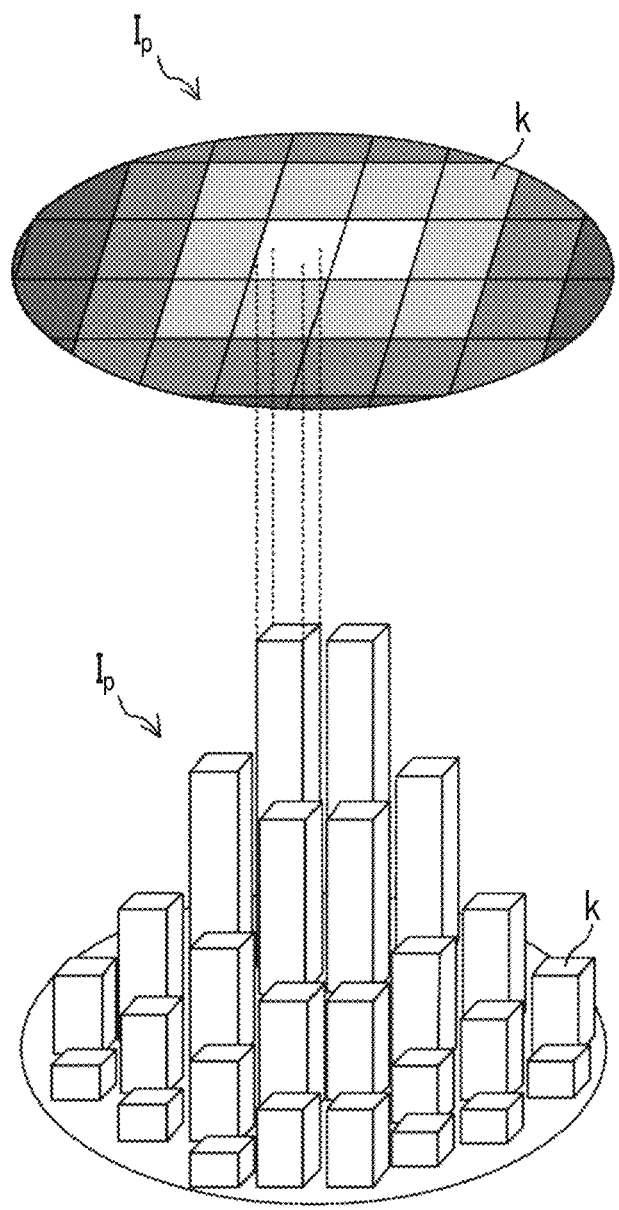
FIG. 5 is a diagram showing a concept of the phase difference image according to the embodiment of the disclosed technology.

Hereinafter, the phase difference image will be described. FIG. 5 is a diagram showing a concept of a phase difference image $I_P$. A lower part of FIG. 5 shows a three-dimensional display of a phase difference amount in each pixel k of the phase difference image $I_P$. The upper part of FIG. 5 shows the phase difference amount in each pixel k of the phase difference image $I_P$ on a plane by gray scale.

Here, the phase difference amount θ in the phase difference image $I_P$ is expressed by Expression (5) in a case in which a phase of a background (region in which the spheres are not present), which is present in the same focal plane of the phase difference image $I_P$ is defined as $θ_B$, and a phase of a region in which the spheres are present is defined as $θ_S$. In addition, the term "phase" in the present specification is a phase of electric field amplitude in a case in which light is regarded as an electromagnetic wave, and is used in more general meaning.

$$θ = θ_S - θ_B \quad (5)$$

In addition, a phase difference amount $θ_k$ in each pixel k of the phase difference image $I_P$ can be expressed by Expression (6). Note that $n_k$ is a refractive index of the sphere at a portion corresponding to each pixel k of the phase difference image $I_P$, $d_k$ is a thickness of the sphere at a portion corresponding to each pixel k of the phase difference image $I_P$, and λ is a wavelength of the object light in the hologram optical system.

$$θ_k = 2π \frac{n_k \cdot d_k}{λ} \quad (6)$$

The phase difference image of the sphere is an image showing distribution of optical path lengths of the object light transmitted through the sphere. Since the optical path length in the sphere corresponds to the product of the refractive index of the sphere and the thickness of the sphere, the phase difference image of the sphere includes information on the refractive index and thickness (shape) of the sphere as shown in Expression (6).

As shown in FIG. 1, since the arrangement of the plurality of spheres 300 flowing inside the flow cell 200 is random, in the phase difference image for each position z in the optical axis direction (z direction) of the imaging apparatus 10, which is generated by the phase difference image generation unit 22, a state is assumed in which at least some of the plurality of spheres partially overlap with each other in the direction of the plane (xy plane) intersecting (orthogonal to) the optical axis direction (z direction) of the imaging apparatus 10. In order to use the phase difference image for evaluation of the individual sphere, it is necessary to separate the plurality of spheres in a state of partially overlapping with other and recognize the spheres as separate spheres. Therefore, the specifying unit 23 specifies a range (region) in the xy plane in which an individual sphere extends in the phase difference image in which the plurality of spheres including the spheres in the state of overlapping with other spheres in the direction of the xy plane is captured.

Specifically, the specifying unit 23 generates an averaged image obtained by averaging at least some of the phase difference images for each position z in the optical axis direction (z direction) of the imaging apparatus 10, and specifies a plurality of image ranges in the direction of the xy plane corresponding to the plurality of spheres in this averaged image. The function of the specifying unit 23 will be described below in more detail. As shown in FIG. 3, the specifying unit 23 includes the addition average image generation unit 24, the inscribed circle derivation unit 25, and the expansion processing unit 26.

Figure 6:
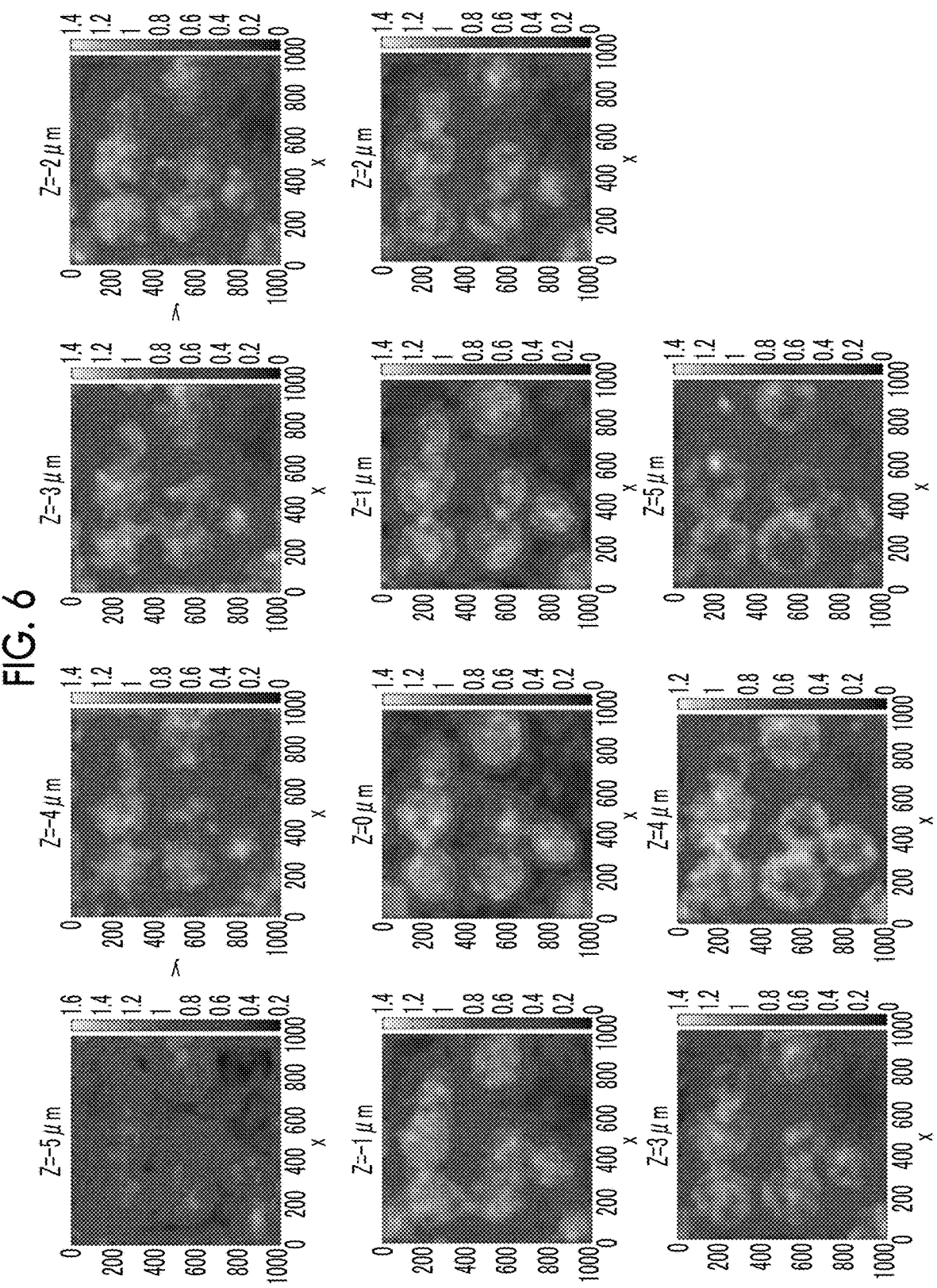
FIG. 6 is a diagram showing an example of a phase difference image at positions different from each other in an optical axis direction according to the embodiment of the disclosed technology.

The addition average image generation unit 24 generates, as the averaged image described above, an addition average image obtained by adding and averaging (additive averaging) the phase difference images at the positions z different from each other in the optical axis direction (z direction) of the imaging apparatus 10. Here, FIG. 6 is a diagram showing an example of the phase difference images generated by the phase difference image generation unit 22 at the positions z different from each other in the optical axis direction (z direction) of the imaging apparatus 10. In the example shown in FIG. 6, the position at which z=0 corresponds to a center position of the sphere in the optical axis direction (z direction) of the imaging apparatus 10. Note that in the example shown in FIG. 6, the phase difference image in which the position z in the optical axis direction (z direction) of the imaging apparatus 10 is changed from −5 μm to 5 μm by 1 μm steps is shown, but the pitch width of the position z and the range of the position z in the phase difference image generated by the phase difference image generation unit 22 are not limited to this example.

The addition average image generation unit 24 generates an addition average image obtained by adding and averaging the phase difference images at the positions z different from each other in the optical axis direction (z direction) of the imaging apparatus 10 as shown in FIG. 6. The sharpness of the outer edge of each sphere differs depending on the positions z in the optical axis direction (z direction) of the imaging apparatus 10 as shown in FIG. 6. Therefore, in a case in which only one phase difference image at the specific position z in the optical axis direction (z direction) of the imaging apparatus 10 is used in a case in which the specifying unit 23 specifies the region of the sphere, the specific accuracy of the region of the sphere may be reduced. By using the addition average image obtained by adding and averaging the phase difference images at the positions z different from each other in the optical axis direction (z direction) of the imaging apparatus 10 in a case in which the specifying unit 23 specifies the region of the sphere, it is possible to improve the specific accuracy of the region of the sphere. Note that the addition average image generation unit 24 may generate the addition average image by using some of a plurality of the phase difference images at the positions z different from each other in the optical axis direction (z direction) of the imaging apparatus 10, which are generated by the phase difference image generation unit 22, or may generate the addition average image by using all of the phase difference images.

The inscribed circle derivation unit 25 derives a plurality of inscribed circles inscribed in an outline with each point at which a distance from the outline corresponding to the outer edge of the sphere in the addition average image is longer than those of other surrounding points as a center. Specifically, the inscribed circle derivation unit 25 derives the inscribed circle by, for example, performing the following processing.

Figure 7A:
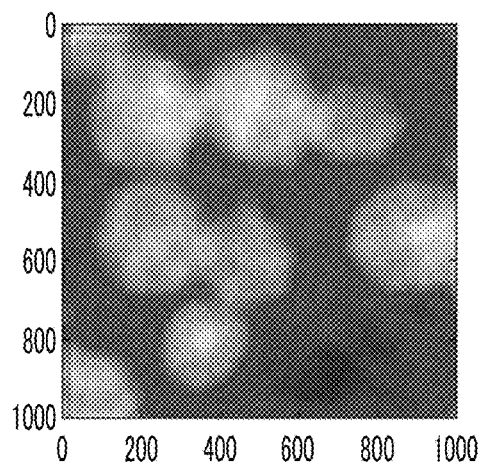
FIG. 7A is a diagram showing an example of an addition average image according to the embodiment of the disclosed technology.
Figure 7B:
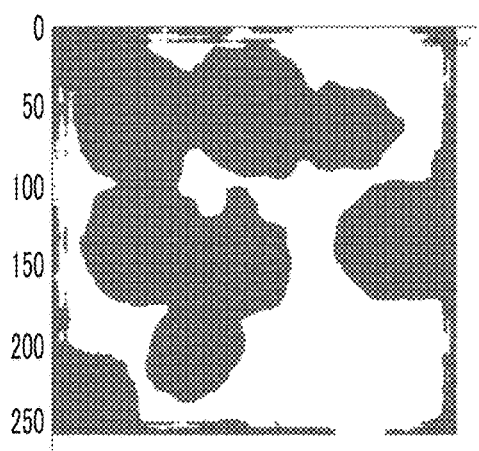
FIG. 7B is a diagram showing an example of an image after binarization processing according to the embodiment of the disclosed technology.

First, the inscribed circle derivation unit 25 performs binarization processing on the addition average image shown in FIG. 7A generated by the addition average image generation unit 24. FIG. 7B is a diagram showing an example of the image after the binarization processing.

Figure 7C:
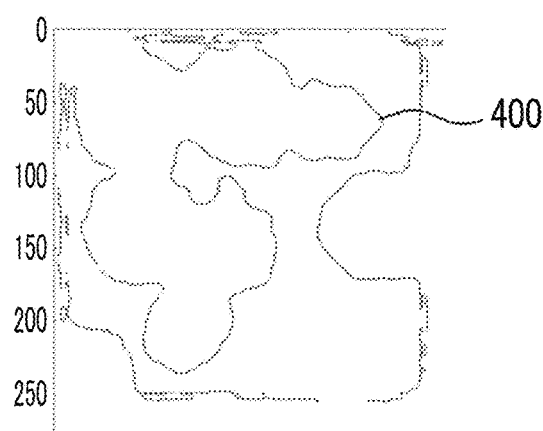
FIG. 7C is a diagram showing an example of an outline according to the embodiment of the disclosed technology.

Next, the inscribed circle derivation unit 25 extracts the outline corresponding to the outer edge of the sphere from the image after the binarization processing. FIG. 7C is a diagram showing an example of an outline 400 extracted from the image after the binarization processing.

Figure 7D:
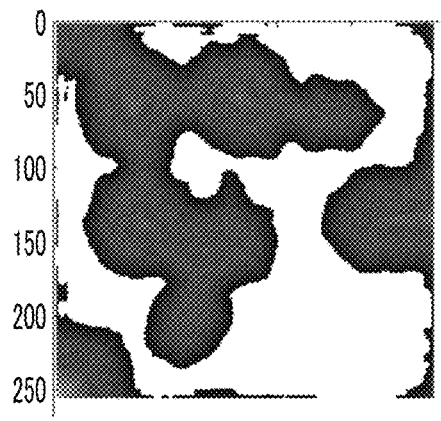
FIG. 7D is an image of a distance function according to the embodiment of the disclosed technology.
Figure 7E:
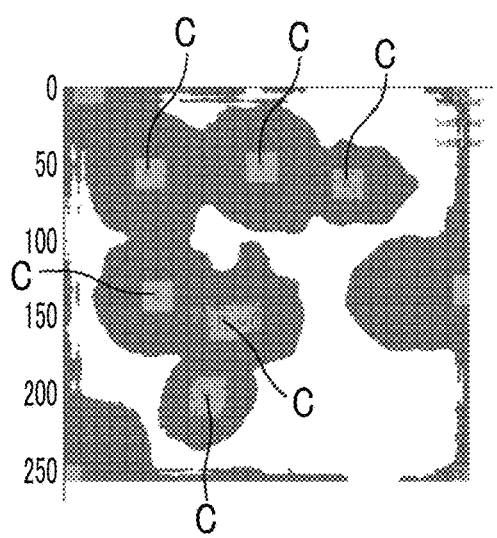
FIG. 7E is a diagram showing an example of a plurality of points at which a distance from the outline according to the embodiment of the disclosed technology is longer than those of other surrounding points.

Next, the inscribed circle derivation unit 25 uses a distance function F (x, y) to extract a plurality of points at which the distance from the extracted outline 400 is longer than those of other surrounding points. The distance function F (x, y) is obtained by deriving the distance between a coordinate (x, y) and the point on the outline 400 at the position at which the distance from the coordinate (x, y) of any pixel in the image is the shortest, for each pixel of an inner region of the outline 400. Incidentally, the point at which the distance function F (x, y)=0 is the point on the outline. FIG. 7D is an image of the distance function F (x, y). FIG. 7E is a diagram showing an example of a plurality of points C at which the distance from the outline 400 is longer than those of other surrounding points, which is extracted based on the distance function P (x, y).

Figure 7F:
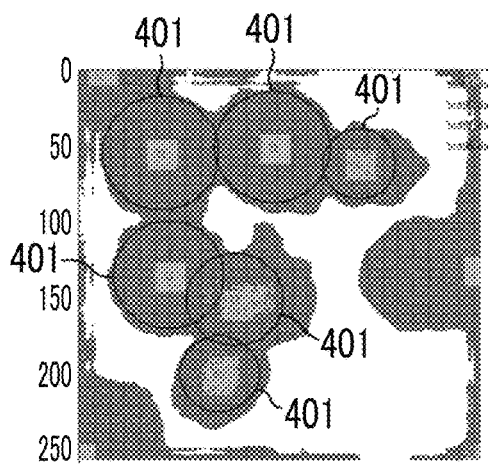
FIG. 7F is a diagram showing an example of a plurality of inscribed circles according to the embodiment of the disclosed technology.

Next, the inscribed circle derivation unit 25 derives the plurality of inscribed circles inscribed in the outline 400 with each of the extracted plurality of points C as a center. FIG. 7F is a diagram showing an example of a derived plurality of inscribed circles 401.

Figure 7G:
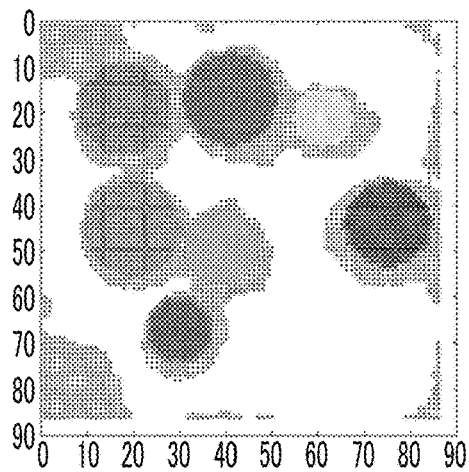
FIG. 7G is a diagram showing an example of an inscribed circle before expansion processing according to the embodiment of the disclosed technology.
Figure 7H:
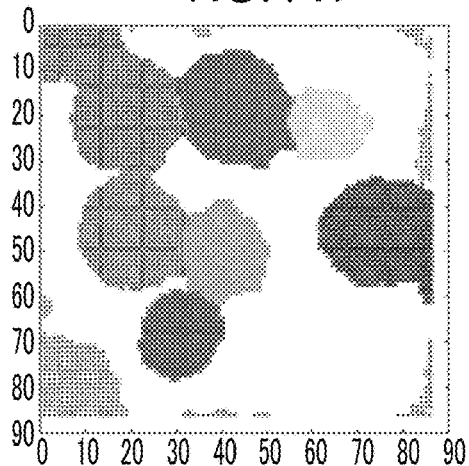
FIG. 7H is a diagram showing an example of an image after the expansion processing according to the embodiment of the disclosed technology.

The expansion processing unit 26 performs expansion processing on each of the inscribed circles 401 derived by the inscribed circle derivation unit 25. Specifically, the expansion processing unit 26 performs, for example, the following processing. First, the expansion processing unit 26 fills each of the inscribed circles 401 before the expansion processing as shown in FIG. 7G. Subsequently, in a case in which there is an unfilled pixel among eight pixels adjacent to each other, which have been already filled, the expansion processing unit 26 fills the unfilled pixel. By repeating this processing by the expansion processing unit 26, a filled region is expanded. The expansion processing unit 26 performs the above expansion processing in parallel with all of the inscribed circles 401 derived by the inscribed circle derivation unit 25. The expansion processing unit 26 terminates the expansion processing in the pixel in a case in which the filled regions derived from the inscribed circles 401 different from each other collide with each other and in a case in which the filled region reaches the outline 400. FIG. 7H is a diagram showing an example of an image after the expansion processing. Each of the filled regions after the expansion processing is the image range corresponding to each of the plurality of spheres.

By performing the processing described above by the specifying unit 23 including the addition average image generation unit 24, the inscribed circle derivation unit 25, and the expansion processing unit 26, the range (region) in the xy plane in which the individual sphere extends in the phase difference image in which the plurality of spheres including the spheres in the state of overlapping with other spheres in the direction of the xy plane is captured is specified.

The extraction unit 27 (see FIG. 1) extracts, for each of the image ranges corresponding to each of the spheres specified in the specifying unit 23, the phase difference image at the center position of the sphere in the optical axis direction (z direction) from the phase difference images for each position z in the optical axis direction (z direction) of the imaging apparatus 10 shown in FIG. 6.

From the phase difference image in which the sphere is not focused, accurate information that coincides with an actual condition of the sphere cannot be obtained due to the effect of spreading due to diffraction. In a case in which the cell is evaluated by using a phase difference image, it is preferable to use the phase difference image in which the sphere, which is an evaluation target, is focused. Here, "the sphere is focused" means obtaining the phase difference image sliced near the center of the spherical sphere. More accurate evaluation can be performed by evaluating the sphere by using the phase difference image in which the sphere is focused.

The details of the processing of extracting the phase difference image at the center position in the optical axis direction (z direction) of the sphere by the extraction unit 27 will be described below.

Figure 8:
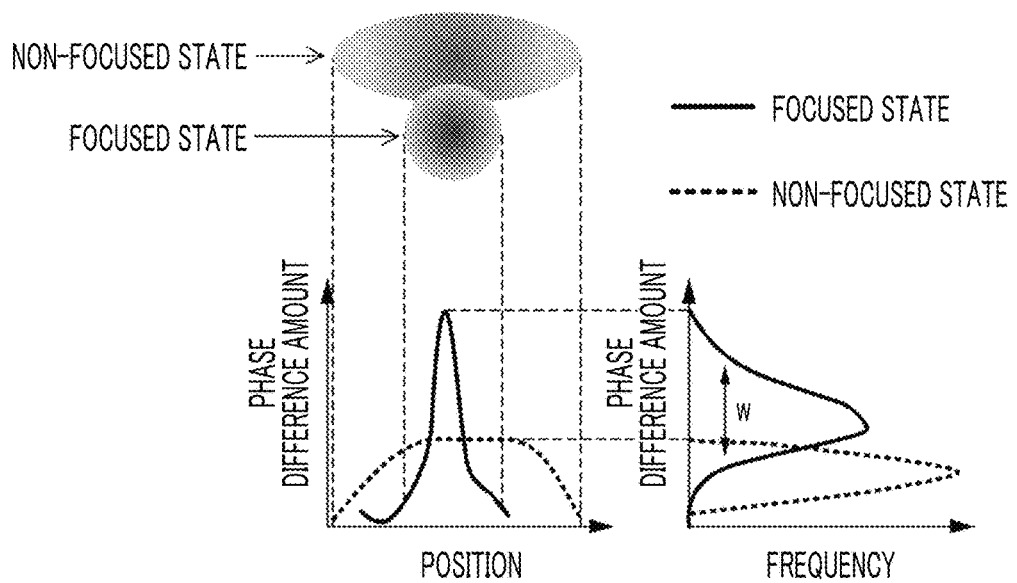
FIG. 8 shows a graph on the left, which shows an example of a relationship between a position in a direction of a plane and a phase difference amount in the phase difference image of the sphere, and a graph on the right, which shows an example of a histogram of the phase difference amount in the phase difference image of the sphere.

A graph on the left of FIG. 8 shows an example of a relationship between the position in a direction of a plane (x direction or y direction) and the phase difference amount in the phase difference image of the sphere, in which the solid line corresponds to a state in which the sphere is not focused and the dotted line corresponds to a state in which the sphere is focused. In a case in which the sphere is focused, a steep peak appears at the specific position in the phase difference image. On the other hand, in a case in which the sphere is not focused, the peak is lower and gentler than a case in which the sphere is focused.

A graph on the right of FIG. 8 shows an example of the histogram of the phase difference amount in the phase difference image of the sphere, in which the solid line corresponds to a state in which the sphere is focused and the dotted line corresponds to a state in which the sphere is not focused. In a case in which the sphere is focused, a curve width w (variation of the phase difference amounts) is relatively large, and in a case in which the sphere is not focused, the curve width w (variation of the phase difference amounts) is relatively small.

Therefore, for each of the phase difference images of the spheres for each of the positions z different from each other in the optical axis direction (z direction) of the imaging apparatus 10, the curve width w (variation of the phase difference amounts) in the histogram of the phase difference amount is obtained, and the phase difference image having the maximum width w among the obtained widths w is extracted as the phase difference image in which the sphere is focused, so that focusing can be realized. The phase difference image having the maximum width w, that is, the phase difference image having the maximum variation of the phase difference amounts corresponds to the phase difference image at the center position of the sphere in the optical axis direction (z direction).

The extraction unit 27, for each of the image ranges (ranges in the xy plane of the spheres) corresponding to each of the spheres specified in the specifying unit 23, performs processing of deriving the variation in the phase difference amount on each of the phase difference images for each position z in the optical axis direction (z direction) of the imaging apparatus 10. For example, the extraction unit 27 may derive a difference between the maximum value and the minimum value of the phase difference amount in the specified image range as the variation of the phase difference amounts in the image range. In addition, the extraction unit 27 may derive a standard deviation of the phase difference amount in the specified image range as the variation of the phase difference amounts in the image range. The extraction unit 27 extracts the image at the position z at which the variation of the phase difference amounts is maximum for each of the specified image ranges.

Figure 9:
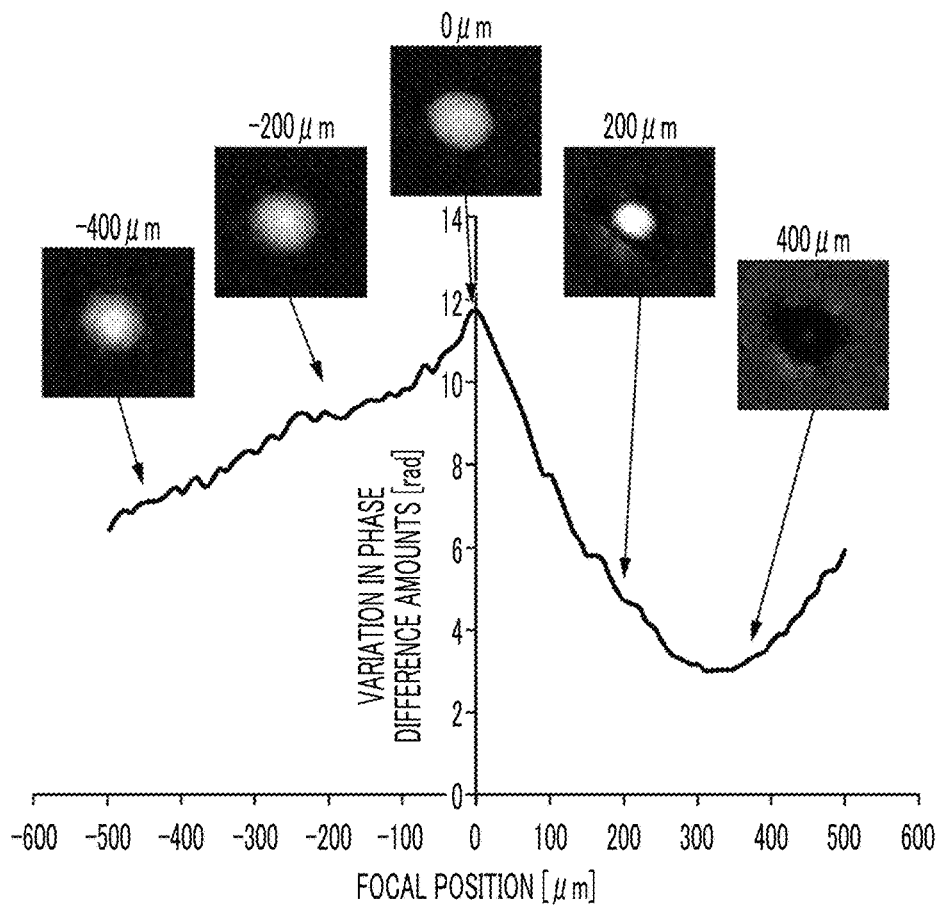
FIG. 9 is a graph showing an example of a relationship between a focal position and a variation of the phase difference amounts in the phase difference image of the sphere.

FIG. 9 is a graph showing an example of a relationship between the focal position (slice position) and the variation of the phase difference amounts in the phase difference image of the sphere. FIG. 9 shows the phase difference images in which the focal positions of the spheres correspond to −400 μm, −200 μm, 0 μm, +200 μm, and +400 μm together with the graph. Note that in FIG. 9, the focal position at which the variation of the phase difference amounts is maximum is set to 0 μm. The phase difference image corresponding to the focal position of 0 μm at which the variation of the phase difference amounts is maximum is extracted as the focused phase difference image. The outline of the sphere is the clearest in the phase difference image corresponding to the focal position 0 μm at which the variation of the phase difference amounts is maximum.

Figure 10:
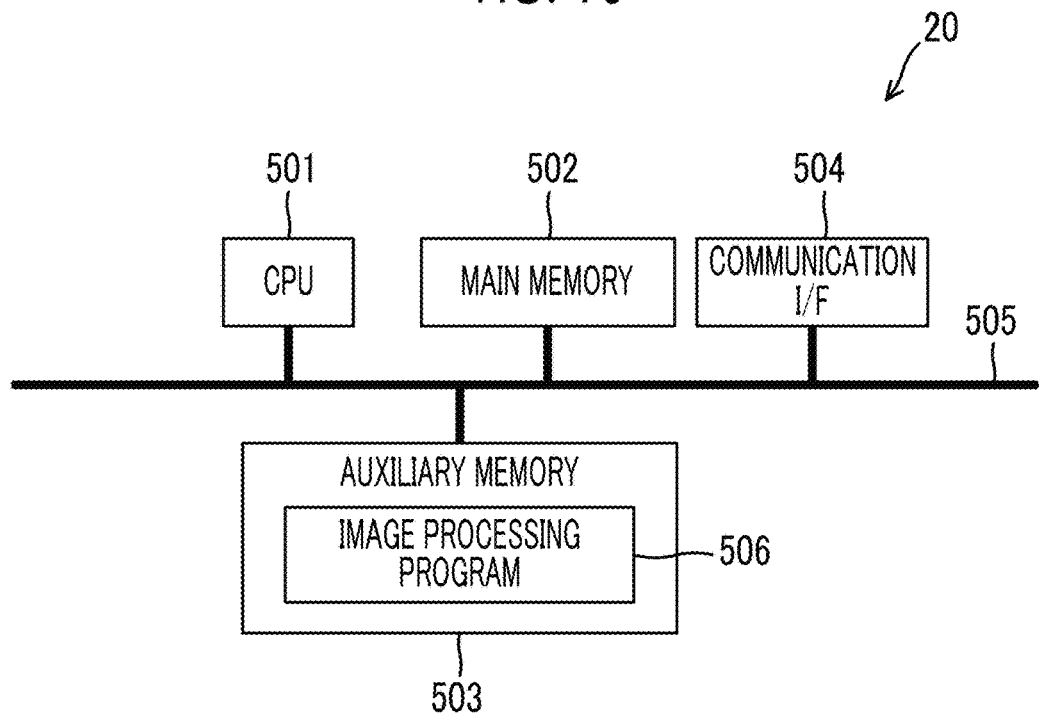
FIG. 10 is an example of a hardware configuration of the image processing apparatus according to the embodiment of the disclosed technology.

FIG. 10 is an example of a hardware configuration of the image processing apparatus 20. The image processing apparatus 20 includes a central processing unit (CPU) 501, a main memory 502 as a transitory storage region, a nonvolatile auxiliary memory 503, and a communication interface 504 that performs communication with other apparatuses including the evaluation apparatus 30 and the imaging apparatus 10. The CPU 501, the main memory 502, the auxiliary memory 503, and the communication interface 504 are each connected to a bus 505.

The auxiliary memory 503 stores an image processing program 506 that causes the CPU 501 to function as the acquisition unit 21, the phase difference image generation unit 22, the specifying unit 23, and the extraction unit 27. The CPU 501 reads out the image processing program 506 from the auxiliary memory 503, develops the readout image processing program 506 in the main memory 502, and sequentially executes the image processing described in the image processing program 506 based on an instruction from an outside supplied via the communication interface 504.

FIG. 11 is a flowchart showing an example of a flow of the image processing described in the image processing program 506.

In step S1, the CPU 501 functions as the acquisition unit 21 and acquires the hologram in which the plurality of spheres are contained within the imaging visual field, which is imaged by the imaging apparatus 10.

In step S2, the CPU 501 functions as the phase difference image generation unit 22 and generates the phase difference images at the positions z different from each other in the optical axis direction (z direction) of the imaging apparatus 10 from the hologram.

In step S3, the CPU 501 functions as the specifying unit 23 (addition average image generation unit 24) and generates the addition average image (see FIG. 6) obtained by adding and averaging the phase difference images at the positions z different from each other in the optical axis direction (z direction) of the imaging apparatus 10.

In step S4, the CPU 501 functions as the specifying unit 23 (inscribed circle derivation unit 25) and performs the binarization processing on the addition average image (see FIG. 7B).

In step S5, the CPU 501 functions as the specifying unit 23 (inscribed circle derivation unit 25) and extracts the outline 400 corresponding to the outer edge of the sphere from the image after the binarization processing (see FIG. 7C).

In step S6, the CPU 501 functions as the specifying unit 23 (inscribed circle derivation unit 25) and specifies the plurality of points C at which the distance from the extracted outline 400 is longer than those of other surrounding points by using the distance function F (x, y) (see FIG. 7E).

In step S7, the CPU 501 functions as the specifying unit 23 (inscribed circle derivation unit 25) and derives the plurality of inscribed circles 401 inscribed in the outline 400 as each of the extracted plurality of points C as a center (see FIG. 7F).

In step S8, the CPU 501 functions as the specifying unit 23 (expansion processing unit 26) and performs the expansion processing on each of the inscribed circles 401. By each of the processing described above, each of the plurality of image ranges in the direction of the plane (xy plane) intersecting the optical axis direction (z direction) of the imaging apparatus 10 corresponding to each of the plurality of spheres is specified. That is, the region in the direction of the xy plane of each of the plurality of spheres which are present with an overlapping portion with other spheres is specified.

In step S9, the CPU 501 functions as the extraction unit 27 and derives the variation of the phase difference amounts for each of the image ranges corresponding to each of the spheres specified in step S8. For example, the CPU 501 may derive the difference between the maximum value and the minimum value of the phase difference amount in the specified image range as the variation of the phase difference amounts in the image range. In addition, the CPU 501 may derive the standard deviation of the phase difference amount in the specified image range as the variation of the phase difference amounts in the image range. The CPU 501 performs the processing described above of deriving the variation of the phase difference amounts for the phase difference images for the positions z in the optical axis direction (z direction) of the imaging apparatus 10 generated in step S2.

In step S10, the CPU 501 functions as the extraction unit 27 and extracts the image at the position z in the optical axis direction at which the variation of the phase difference amounts is maximum for each of the image ranges corresponding to each of the spheres specified in step S8.

The evaluation apparatus 30 evaluates the sphere by using the phase difference image extracted by the extraction unit 27 of the image processing apparatus 20, and outputs an evaluation result.

FIG. 12 is a functional block diagram showing an example of a functional configuration of the evaluation apparatus 30. The evaluation apparatus 30 includes an acquisition unit 31, a shape index value derivation unit 32, a phase difference amount sum derivation unit 33, and a determination unit 34.

The acquisition unit 31 acquires the phase difference image extracted by the extraction unit 27 of the image processing apparatus 20. That is, the acquisition unit 31 acquires the phase difference image at the center position in the optical axis direction (z direction) of the imaging apparatus 10 for each of the plurality of spheres.

The shape index value derivation unit 32 derives a shape index value of the sphere included in the phase difference image acquired by the acquisition unit 31. As the shape index value of the sphere, for example, volume, a cross section area, a particle diameter, a circumference, and the like of the sphere can be used. The particle diameter and the circumference of the sphere can be obtained directly from the phase difference image at the center position of the sphere in the optical axis direction. The cross section area of the sphere can be derived, for example, as a cross section area of a circle of which a diameter is the particle diameter of the sphere. The volume of the sphere can be derived, for example, as the volume of the sphere of which a diameter is the particle diameter of the sphere.

The phase difference amount sum derivation unit 33 derives a phase difference amount sum 6A, which is a value obtained by integrating the phase difference amounts of a plurality of pixels constituting the phase difference image. The phase difference amount sum OA is expressed by Expression (7). Note that s is the area of each pixel k of the phase difference image, and $v_k$ is the volume of the sphere at the portion corresponding to each pixel k of the phase difference image. As shown in Expression (7), the phase difference amount sum BA corresponds to the value obtained by integrating the phase difference amounts $\theta_k$ for the pixels of the phase difference image of the sphere for all of the pixels k. Note that in Expression (7), $d_k$ indicates a thickness of a sphere portion projected on the pixel k, and $n_k$ indicates a refractive index difference between a background culture solution and an inside of the sphere. In Expression (7), $v_k = d_k \cdot s$ is used. Here, according to Expression (7), the unit of the phase difference amount sum $\theta_A$ is the scale of the area, for example, [µm$^2$], but in a case in which no comparison is performed between the image sensors, the unit of the phase difference amount sum $\theta_A$ may simply be [pixel] as the sum of the phase difference amount $\theta_k$ for each pixel per pixel, that is, s=1 [pixel].

$$\theta_A = \sum_{k=1}^{N} \theta_k \cdot s = \frac{2\pi}{\lambda} \sum_{k=1}^{N} n_k \cdot d_k \cdot s = \frac{2\pi}{\lambda} \sum_{k=1}^{N} n_k \cdot v_k \qquad (7)$$

The determination unit 34 compares the correlation between a reference correlation trend line showing a reference of the correlation between the phase difference amount sum $\theta_A$ and the shape index value of the sphere and the correlation between the phase difference amount sum $\theta_A$ and the shape index value for the sphere, which is a determination target, and determines the state of the sphere, which is the determination target, in response to a degree of the deviation of the correlation for the sphere, which is the determination target, from the reference correlation trend line. Note that as the reference correlation trend line can be acquired in advance and used. In a case in which the width of the deviation of the correlation of the sphere, which is the determination target, from the reference correlation trend line exceeds a threshold value, the determination unit 34 may determine that at least one of the viability, the density, or the homogeneity of the cell included in the sphere, or the outer shape of the sphere, which is the determination target, is abnormal.

Figure 13:
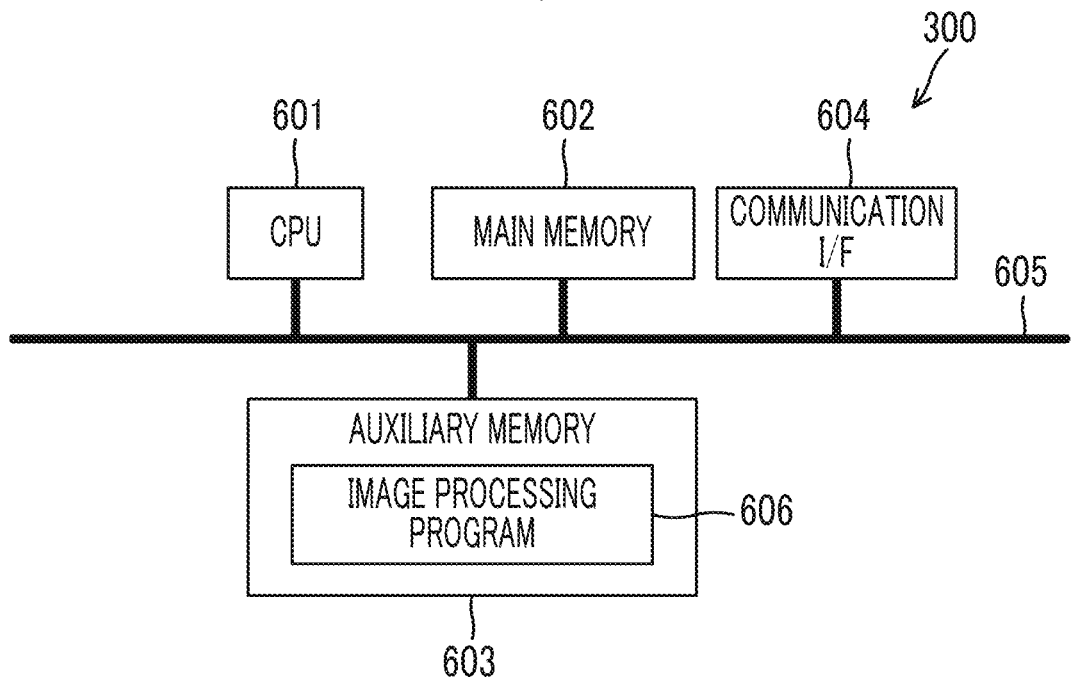
FIG. 13 is an example of a hardware configuration of the evaluation apparatus according to the embodiment of the disclosed technology.

FIG. 13 is an example of a hardware configuration of the evaluation apparatus 30. The evaluation apparatus 30 includes a CPU 601, a main memory 602 as a transitory storage region, a non-volatile auxiliary memory 603, and a communication interface 604 that performs communication with other apparatuses including the image processing apparatus 20. The CPU 601, the main memory 602, the auxiliary memory 603, and the communication interface 604 are each connected to a bus 605.

The auxiliary memory 603 stores an evaluation program 606 that causes the CPU 601 to function as the acquisition unit 31, the shape index value derivation unit 32, the phase difference amount sum derivation unit 33, and the determination unit 34. The CPU 601 reads out the evaluation program 606 from the auxiliary memory 603, develops the readout evaluation program 606 in the main memory 602, and sequentially executes the evaluation processing described in the evaluation program 606 based on an instruction from an outside supplied via the communication interface 604. Note that in the present embodiment, a case is described in which the evaluation apparatus 30 and the image processing apparatus 20 are configured by separate computers, but the evaluation apparatus 30 and the image processing apparatus 20 can also be configured by a common computer.

Figure 14:
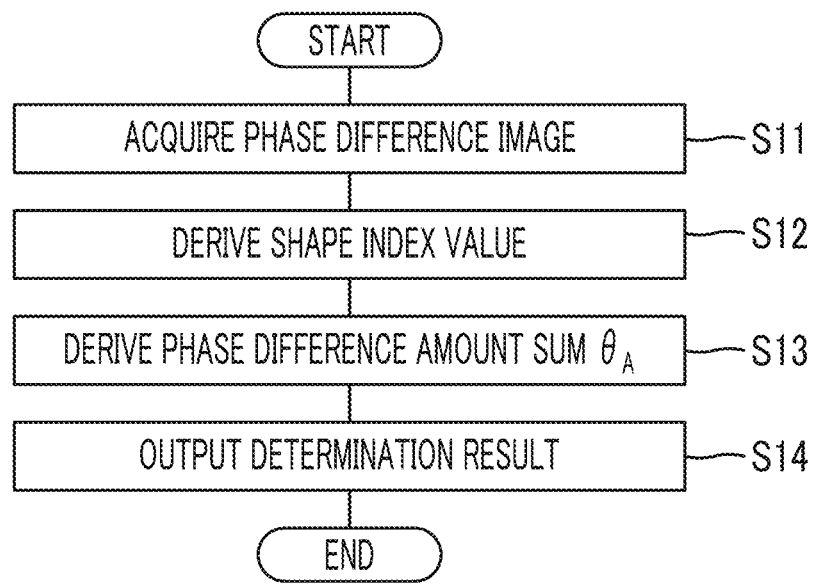
FIG. 14 is a flowchart showing an example of a flow of evaluation processing according to the embodiment of the disclosed technology.

FIG. 14 is a flowchart showing an example of a flow of the evaluation processing described in the evaluation program 606.

In step S11, the CPU 601 functions as the acquisition unit 31 and acquires the phase difference image extracted by the extraction unit 27 of the image processing apparatus 20.

In step S12, the CPU 601 functions as the shape index value derivation unit 32 and derives the shape index value of the sphere included in the phase difference image acquired in step S11. As the shape index value of the sphere, for example, the volume, the cross section area, the particle diameter, the circumference, and the like of the sphere can be used.

In step S13, the CPU 601 functions as the phase difference amount sum derivation unit 33 and derives the phase difference amount sum $\theta_A$ for the phase difference image acquired in step S11.

In step S14, the CPU 601 functions as the determination unit 34, compares the correlation between the reference correlation trend line showing the reference of the correlation between the phase difference amount sum $\theta_A$ and the shape index value of the sphere and the correlation between the phase difference amount sum $\theta_A$ and the shape index value for the sphere, which is a determination target, determines the state of the sphere, which is the determination target, in response to the degree of the deviation of the correlation for the sphere, which is the determination target, from the reference correlation trend line, and outputs a determination result. Note that as the reference correlation trend line can be stored in advance in the auxiliary memory 603 and used. In a case in which the width of the deviation of the correlation of the sphere, which is the determination target, from the reference correlation trend line exceeds the threshold value, the determination unit 34 may determine that at least one of the viability, the density, or the homogeneity of the cell included in the sphere, or the outer shape of the sphere, which is the determination target, is abnormal.

Figure 15:
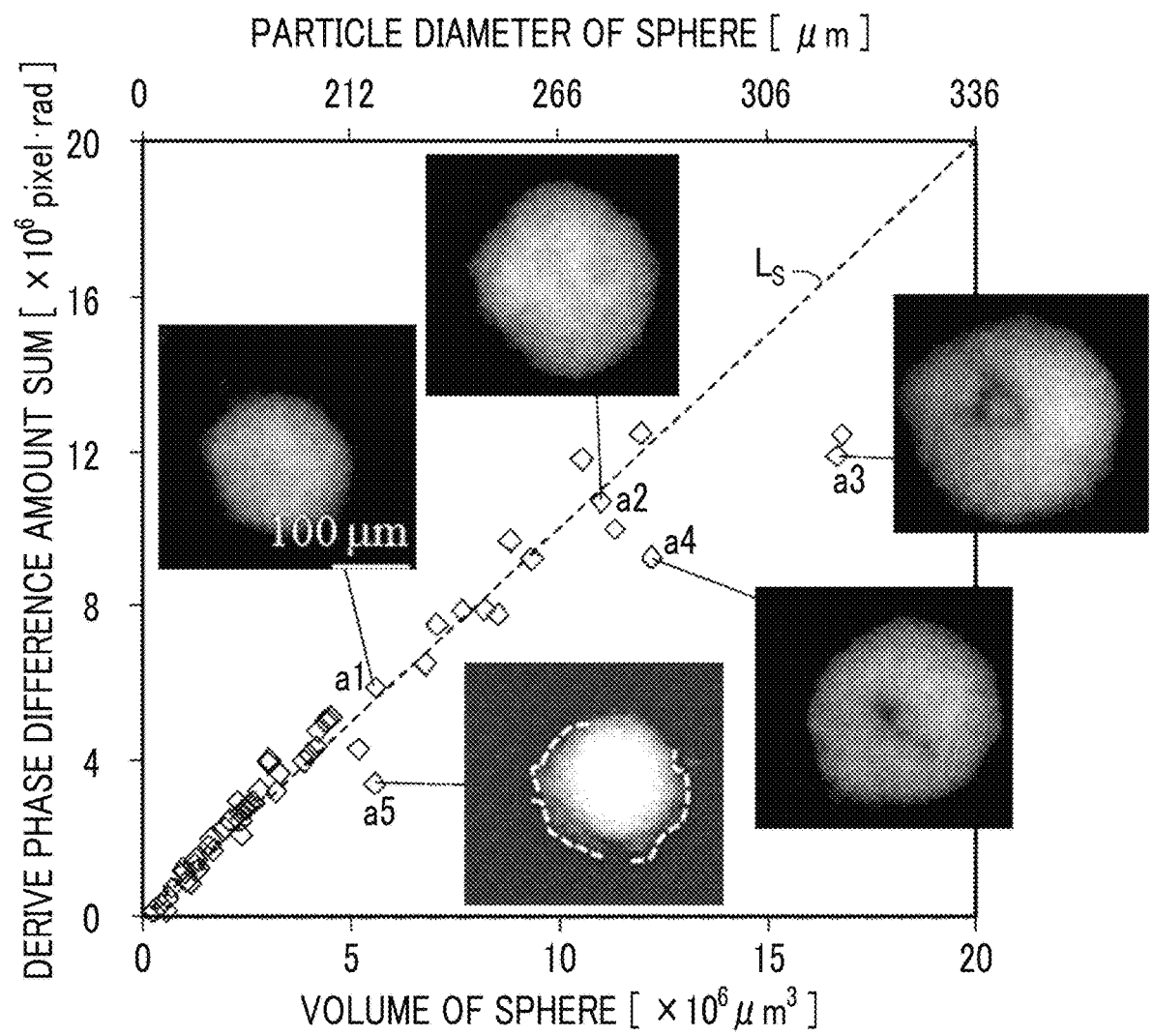
FIG. 15 is a graph showing an example of a correlation characteristic between volume of the sphere and a phase difference amount sum.

FIG. 15 is a graph showing an example of a correlation characteristic between the volume of the sphere and the phase difference amount sum $\theta_A$. As shown in FIG. 15, it is confirmed that the phase difference amount sum $\theta_A$ and the volume of the sphere are in a proportional relationship. In FIG. 15, a reference correlation trend line $L_S$ showing the reference of the correlation between the volume of the sphere and the phase difference amount sum $\theta_A$ is shown together with the plot. The regression line derived from each plot shown in FIG. 15 is applied as the reference correlation trend line $L_S$.

FIG. 15 shows the phase difference images of the spheres corresponding to plots a1 and a2 present on the reference correlation trend line $L_S$ and the phase difference images of the spheres corresponding to plots a3, a4, and a5 present at positions deviating from the reference correlation trend line $L_S$. For the spheres corresponding to the plots a1 and a2 present on the reference correlation trend line $L_S$, the phase difference images having uniform brightness are obtained over the entire sphere. This result indicates that the plurality of cells constituting the sphere are homogeneous, and that the density of cells in the sphere is uniform. On the other hand, for the spheres corresponding to the plots a3 and a4 present at the positions deviating from the reference correlation trend line $L_S$, the phase difference images having the brightness at the central portion, which is decreased as compared with that in other portions are obtained. This result indicates that the plurality of cells constituting the sphere are not homogeneous, and that the density of cells in the sphere is not uniform. In addition, for the sphere corresponding to the plot a5 present at the position deviating from the reference correlation trend line $L_S$, the phase difference image in which the unevenness of the outline of the sphere is remarkable is obtained. This result indicates that the cells constituting the sphere are abnormal.

From the results described above, it can be said that the state of the sphere can be determined by using the correlation between the phase difference amount sum $\theta_A$ and the volume, which is an example of the shape index value of the sphere. In addition, it is possible to compare the correlation between a reference correlation trend line $L_S$ showing the correlation between the phase difference amount sum $\theta_A$ and the volume of the sphere and the correlation between the phase difference amount sum $\theta_A$ and the shape index value for the sphere, which is a determination target, and determine the state of the sphere in response to the degree of the deviation of the correlation for the sphere, which is the determination target, from the reference correlation trend line $L_S$. Specifically, it is possible to determine the state of each sphere in response to the degree of the deviation of the reference correlation trend line $L_S$ from the plots for the sphere, which is the determination target, plotted on a graph on which one axis is the volume of the sphere and the other axis is the phase difference amount sum $\theta_A$. Therefore, for example, for the sphere of which a minus width of the phase difference amount sum $\theta_A$ from the reference correlation trend line $L_S$ is equal to or greater than a threshold value, it can be determined that at least one of the density, the homogeneity, or the outer shape of the sphere of the cell included in the sphere is abnormal.

Note that in the present embodiment, the volume of the sphere is used as the shape index value of the sphere, but instead of the volume, the cross section area, the particle diameter, or the circumference of the sphere can be used. Regardless of which of these shape index values is used, it is possible to determine the state of the sphere by using the correlation with the phase difference amount sum $\theta_A$.

Figure 16:
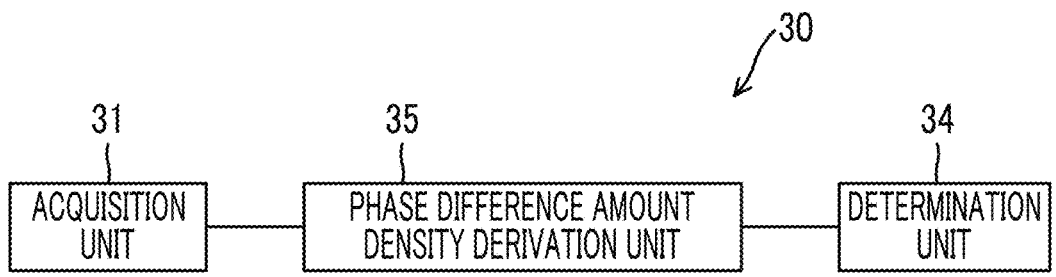
FIG. 16 is a functional block diagram showing another example of the functional configuration of the evaluation apparatus according to the embodiment of the disclosed technology.

Other aspects of the evaluation apparatus 30 will be described below. FIG. 16 is a functional block diagram showing another example of the functional configuration of the evaluation apparatus 30. The evaluation apparatus 30 includes the acquisition unit 31, a phase difference amount density derivation unit 35, and the determination unit 34. In the present embodiment, the evaluation apparatus 30 derives a phase difference amount density $D_P$ obtained by dividing the phase difference amount sum $\theta_A$ by the volume of the sphere, and determines the state of the sphere based on the derived phase difference amount density $D_P$.

The phase difference amount density $D_P$ is expressed by Expression (8). Note that V is the volume of the sphere. As shown in Expression (8), the phase difference amount density $D_P$ corresponds to the phase difference amount sum $\theta_A$ divided by the volume V of the sphere. Due to homeostasis, healthy cells are considered to maintain a fixed value of internal refractive index, which is different from the refractive index of a medium. On the other hand, it is considered that dead cells lose homeostasis and the internal refractive index is substantially the same as the refractive index of the medium. Therefore, it is considered that the phase difference amount density $D_P$ can be used as an index indicating the state of the cell. For example, in a case in which the phase difference amount density $D_P$ acquired for the sphere, which is the determination target, is equal to or greater than a threshold value, it can be determined that the state of the sphere is good, and in a case in which the phase difference amount density $D_P$ is less than the threshold value, it can be determined that the state of the sphere is abnormal. Note that since $2\pi/k$ can be treated as a fixed value, the multiplication of $2\pi/k$ may be omitted in a case of deriving the phase difference amount density $D_P$. Here, in a case in which a volume average refractive index difference $N_{ave}$ of the sphere is $N_{ave} = \Sigma n_k \cdot (v_k/V)$, Expression (8) is $D_P = (2\pi/\lambda) \times N_{ave}$, the phase difference amount density is the refractive index difference of the volume-averaged sphere normalized by a wavelength length. In the present specification, V is obtained by calculating an equivalent sphere diameter from a cross section image of a phase image of the sphere. It is also possible to obtain an ellipsoidal sphere more accurately.

$$D_P = \frac{\theta_A}{V} = \frac{2\pi}{\lambda} \sum_{k=1}^{N} n_k \cdot \frac{v_k}{V} \quad (8)$$

Figure 17:
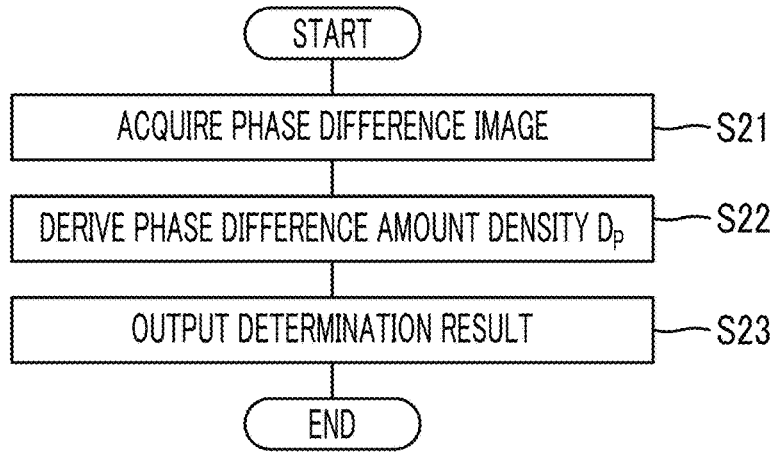
FIG. 17 is a flowchart showing another example of the flow of the evaluation processing according to the embodiment of the disclosed technology.

The hardware configuration of the evaluation apparatus 30 according to the present embodiment is the same as that shown in FIG. 13. FIG. 17 is a flowchart showing another example of the flow of the evaluation processing described in the evaluation program 606 according to the present embodiment.

In step S21, the CPU 601 functions as the acquisition unit 31 and acquires the phase difference image extracted by the extraction unit 27 of the image processing apparatus 20.

In step S22, the CPU 601 functions as the phase difference amount density derivation unit 35 and derives the phase difference amount density $D_P$ for the phase difference image acquired in step S21.

In step S23, the CPU 601 functions as the determination unit 34, estimates the cell viability in the sphere based on a correlation line showing the correlation between the cell viability and the phase difference amount density $D_P$, which is acquired in advance, and the phase difference amount density $D_P$ derived in step S22, and outputs the determination result.

Figure 18:
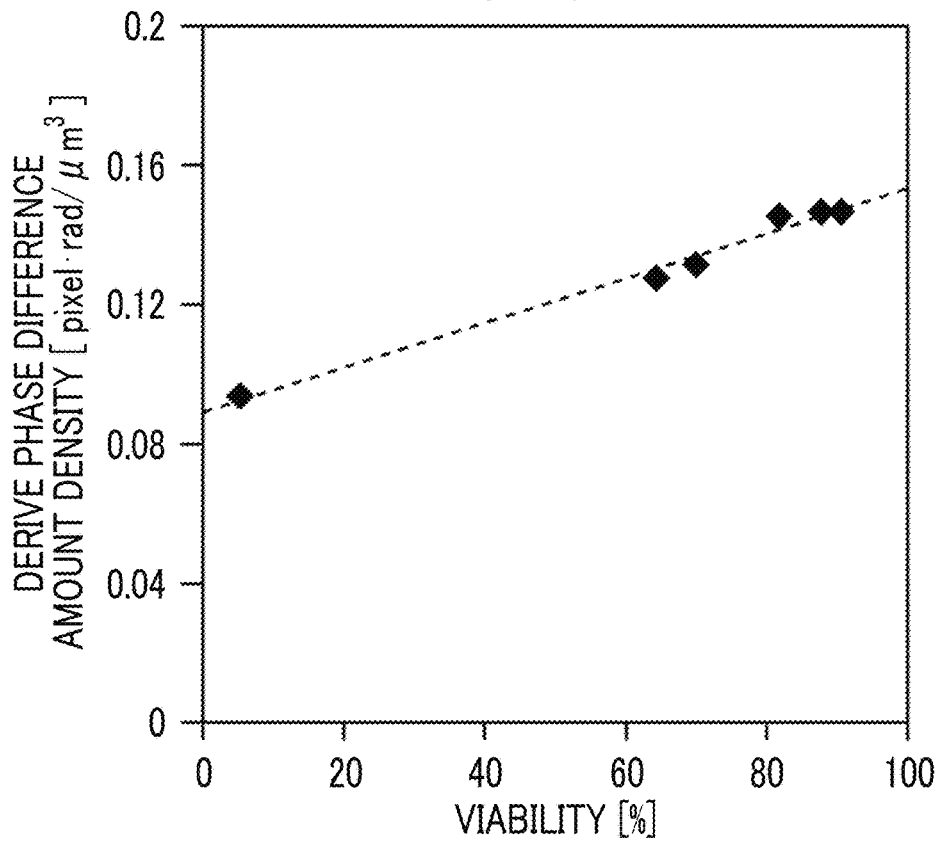
FIG. 18 is a graph showing an example of a correlation characteristic between cell viability of and a phase difference amount density.

FIG. 18 is a graph showing an example of a correlation characteristic between cell viability and the phase difference amount density $D_P$ (lot average value). A procedure for measurement of the viability is as follows. The spheres housed in a centrifuge tube are subjected to centrifugation processing at 400 G for 3 minutes. The spheres precipitated at the bottom of the centrifuge tube are collected and decomposed into single cells by using TrypLE (registered trademark) Select, which is cell dissociation enzyme. By performing to dead cell staining processing with Trypan Blue on the decomposed cells and then counting the cells with a general commercially available cell counter (Countess (registered trademark)), the number of stained dead cells is counted. The cell viability is derived for each culture lot from the count number of dead cells.

By forming the plot for each culture lot on a graph on which a horizontal axis is the cell viability and a vertical axis is the phase difference amount density $D_P$, the correlation characteristic between the cell viability and the phase difference amount density $D_P$ (lot average value) is acquired. As shown in FIG. 18, it is confirmed that the cell viability and the phase difference amount density $D_P$ are in a proportional relationship.

From the results described above, it can be said that the cell viability can be estimated from the phase difference amount density $D_P$. By estimating the cell viability from the phase difference amount density $D_P$, the cell viability can be grasped without performing processing involving cell destruction, such as the centrifugation processing and the staining processing (that is, non-destructively). The evaluation apparatus 30 according to the present embodiment outputs the cell viability in the culture lot estimated from the correlation line showing the correlation between the cell viability and the phase difference amount density $D_P$ and the average value of the phase difference amount density $D_P$ acquired for the sphere belonging to the culture lot, which is the determination target, as the determination result.

As described above, with the evaluation system 1 according to the embodiment of the disclosed technology, it is assumed that in the phase difference image generated by the phase difference image generation unit 22, at least some of the plurality of spheres partially overlap with each other in the direction of the plane (xy plane) intersecting the optical axis direction (z direction) of the imaging apparatus 10. In order to use the phase difference image for evaluation of the individual sphere, it is necessary to separate the plurality of spheres in the state of partially overlapping with other in the phase difference image and recognize the spheres as separate spheres.

With the image processing apparatus 20 according to the embodiment of the disclosed technology, the phase difference image generation unit 22 generates the phase difference images at the positions different from each other in the optical axis direction (z direction) of the imaging apparatus 10 from the hologram imaged by the imaging apparatus 10, the specifying unit 23 specifies the plurality of image ranges in the direction of the xy plane corresponding to the plurality of spheres in the addition average image obtained by adding and averaging the phase difference images, and the extraction unit 27 extracts the phase difference image at the center position in the optical axis direction (z direction) of the corresponding sphere in each of the specified image ranges. That is, the specifying unit 23 specifies the range (region) in the xy plane in which the individual sphere extends, and the extraction unit 27 extracts the appropriately focused phase difference image for an extend range (region) of each sphere. Therefore, with the image processing apparatus 20, it is possible to appropriately perform the evaluation the state of each sphere.

In addition, with the evaluation system 1 according to the embodiment of the disclosed technology, each of the plurality of spheres is evaluated based on the hologram obtained by imaging the plurality of spheres contained within the imaging visual field, so that it is possible to significantly shorten the processing time as compared with the evaluation method in the related art using flow cytometry. That is, with the evaluation system 1, a large amount of the spheres can be evaluated non-destructively and quickly.

Note that in the above description, a case has been described in which the state of the sphere, which is the aggregate of the cells, is evaluated, but the disclosed technology can be applied to a case in which the granule other than the sphere is evaluated. In addition, a case has been described in which the specifying unit 23 uses the averaged image and the addition average image used in a case of specifying the image range corresponding to each of the spheres, but a geometric mean image obtained by synergistically averaging at least some of the phase difference images may be used as the averaged image, or a weighted averaged image obtained by weighted averaging at least some of the phase difference images may be used as the averaged image.

EXPLANATION OF REFERENCES

1: evaluation system
10: imaging apparatus
20: image processing apparatus
21: acquisition unit
22: phase difference image generation unit
23: specifying unit
24: addition average image generation unit
25: inscribed circle derivation unit
26: expansion processing unit
27: extraction unit
30: evaluation apparatus
31: acquisition unit
32: shape index value derivation unit
33: phase difference amount sum derivation unit
34: determination unit
35: phase difference amount density derivation unit
100: hologram optical system
101: laser light source
102: beam splitter
103: collimating lens
105: objective lens
107: imaging lens
108: beam splitter
109: optical fiber
110: collimating lens
200: flow cell
300: sphere
400: outline
401: inscribed circle
501, 601: CPU
502, 602: main memory
503, 603: auxiliary memory
504, 604: communication interface
505, 605: bus
506: image processing program
606: evaluation program

What is claimed is:
1. An image processing apparatus comprising:
an acquisition unit that acquires a hologram obtained by imaging a plurality of granules contained within an imaging visual field;
a generation unit that generates, from the hologram, phase difference images at positions different from each other in an optical axis direction in a case in which the hologram is captured;
a specifying unit that specifies a plurality of image ranges in a direction of a plane intersecting the optical axis direction, which correspond to the plurality of granules, in an averaged image obtained by averaging at least some of the phase difference images; and an extraction unit that extracts the phase difference image at a center position of a corresponding granule in the optical axis direction for each of the plurality of image ranges.

2. The image processing apparatus according to claim 1, wherein the specifying unit includes
an addition average image generation unit that generates, as the averaged image, an addition average image obtained by adding and averaging at least some of the phase difference images,
an inscribed circle derivation unit that derives a plurality of inscribed circles inscribed in an outline corresponding to an outer edge of the granule in the addition average image with each point at which a distance from the outline is longer than those of other surrounding points as a center, and
an expansion processing unit that performs expansion processing on each of the inscribed circles.

3. The image processing apparatus according to claim 1, wherein the extraction unit extracts, as the phase difference image at the center position of the granule in the optical axis direction, a phase difference image having a maximum variation of phase difference amounts between pixels among the phase difference images at the positions different from each other in the optical axis direction.

4. The image processing apparatus according to claim 2, wherein the extraction unit extracts, as the phase difference image at the center position of the granule in the optical axis direction, a phase difference image having a maximum variation of phase difference amounts between pixels among the phase difference images at the positions different from each other in the optical axis direction.

5. The image processing apparatus according to claim 1, wherein the granule is an aggregate of a plurality of cells.

6. The image processing apparatus according to claim 2, wherein the granule is an aggregate of a plurality of cells.

7. The image processing apparatus according to claim 3, wherein the granule is an aggregate of a plurality of cells.

8. An evaluation system comprising:
an imaging apparatus that captures a hologram in which a plurality of granules are contained within an imaging visual field;
an image processing apparatus that performs image processing on the hologram; and
an evaluation apparatus that outputs an evaluation result for each of the plurality of granules based on an image obtained by the image processing apparatus,
wherein the image processing apparatus includes
an acquisition unit that acquires the hologram,
a generation unit that generates, from the hologram, phase difference images at positions different from each other in an optical axis direction in a case in which the hologram is captured,
a specifying unit that specifies a plurality of image ranges in a direction of a plane intersecting the optical axis direction, which correspond to the plurality of granules, in an averaged image obtained by averaging at least some of the phase difference images, and
an extraction unit that extracts the phase difference image at a center position of a corresponding granule in the optical axis direction for each of the plurality of image ranges, and
the evaluation apparatus derives the evaluation result by using the phase difference image extracted by the extraction unit.

9. The evaluation system according to claim 8, further comprising:
a flow passage through which the plurality of granules flow,
wherein the imaging apparatus is installed such that an entire region of the flow passage in a width direction is contained within the imaging visual field.

10. A non-transitory computer readable recording medium storing an image processing program causing a computer to execute a process comprising:
acquiring a hologram obtained by imaging a plurality of granules contained within an imaging visual field;
generating, from the hologram, phase difference images at positions different from each other in an optical axis direction in a case in which the hologram is captured;
specifying a plurality of image ranges in a direction of a plane intersecting the optical axis direction, which correspond to the plurality of granules, in an averaged image obtained by averaging at least some of the phase difference images; and
extracting the phase difference image at a center position of a corresponding granule in the optical axis direction for each of the plurality of image ranges.

11. An image processing method comprising:
acquiring a hologram obtained by imaging a plurality of granules contained within an imaging visual field;
generating, from the hologram, phase difference images at positions different from each other in an optical axis direction in a case in which the hologram is captured;
specifying a plurality of image ranges in a direction of a plane intersecting the optical axis direction, which correspond to the plurality of granules, in an averaged image obtained by averaging at least some of the phase difference images; and
extracting the phase difference image at a center position of a corresponding granule in the optical axis direction for each of the plurality of image ranges.

* * * * *